(12) United States Patent
Canton et al.

(10) Patent No.: US 10,150,946 B2
(45) Date of Patent: Dec. 11, 2018

(54) MEDIA FOR STEM CELLS

(71) Applicant: The University of Sheffield, Sheffield (GB)

(72) Inventors: Irene Canton, Sheffield (GB); Steven Peter Armes, Sheffield (GB); Nicholas John Warren, Sheffield (GB); Harry Moore, Sheffield (GB); Giuseppe Battaglia, London (GB); Denis Cecchin, London (GB)

(73) Assignee: The University of Sheffield, Sheffield, South Yorkshire (GB)

( * ) Notice: Subject to any disclaimer, the term of this patent is extended or adjusted under 35 U.S.C. 154(b) by 0 days.

(21) Appl. No.: 14/769,724

(22) PCT Filed: Feb. 21, 2014

(86) PCT No.: PCT/GB2014/050541
§ 371 (c)(1),
(2) Date: Aug. 21, 2015

(87) PCT Pub. No.: WO2014/128500
PCT Pub. Date: Aug. 28, 2014

(65) Prior Publication Data
US 2015/0376567 A1 Dec. 31, 2015

(30) Foreign Application Priority Data

Feb. 21, 2013 (GB) .................................. 1303101.8

(51) Int. Cl.
*C12N 5/00* (2006.01)

(52) U.S. Cl.
CPC ........ *C12N 5/0068* (2013.01); *C12N 2533/40* (2013.01); *C12N 2539/10* (2013.01)

(58) Field of Classification Search
CPC ............ C12N 2533/40; C12N 2539/10; C12N 5/0068
See application file for complete search history.

(56) References Cited

U.S. PATENT DOCUMENTS

| | | | |
|---|---|---|---|
| 6,103,528 A | 8/2000 | An et al. | |
| 2007/0037281 A1* | 2/2007 | Kruse ................... | C12N 5/0677 435/366 |
| 2009/0143830 A1* | 6/2009 | Bourgeois ............... | A61L 27/46 606/86 R |
| 2010/0227819 A1* | 9/2010 | Hernandez ............. | C07K 14/61 514/1.1 |
| 2010/0266553 A1* | 10/2010 | Ra ........................ | C12N 5/0605 424/93.7 |

FOREIGN PATENT DOCUMENTS

| | | |
|---|---|---|
| WO | 2007063320 A1 | 6/2007 |
| WO | 2009065123 A1 | 5/2009 |
| WO | 2012172291 A1 | 12/2012 |
| WO | 2013017825 A1 | 2/2013 |

OTHER PUBLICATIONS

Ghanami et al. Soft Matter (2010) 6: 5037-5044.*
Sun et al. Langmuir (2010) 26(11): 8015-8020 (Year: 2010) (Year: 2010).*
Ultrafiltration membranes from www.con-servwater-UF.html, downloaded Dec. 22, 2017 (Year: 2017).*
Zhang et al. J. Biomaterials Science (2010) 21: 253-269 (Year: 2010).*
Loh et al. J. Phys. Chem. (2009) 113: 11822-11830 (Year: 2009).*
Adam Blanazs et al: "Sterilizable Gels from Thermoresponsive Block Copolymer Worms" Journal of the American Chemical Society, vol. 134. No. 23 Jun. 13, 2012 (Jun. 13, 2012) pp. 9741-9748. XP055119573.
International Search Report and Written Opinion for Application No. PCT/GB2014/050541 dated Jun. 4, 2014.
Ken Kataoka et al: "Application of a thermo-reversible gelation polymer, Mebiol Gel, for Stem cell culture and regenerative medicine", Journal of Stem cells & Regenerative Medicine, vol. 6, No. 1, Jan. 1, 2010 (Jan. 1, 2010), pp. 10-14, XP055119724, Retrieved from the Internet: URL:http://www.ncbi.nlm.nih.gov/pmc/articles/PMC3908250/pdf/jsrm-06-010.pdf [retrieved on May 23, 2014].
Lapworth et al., "Thermally reversible colloidal gels for three-dimensional chondrocyte culture", J Royal Soc Interface; vol. 9, pp. 362-375 (2012), See entire document, especially Results and Discussion.
Search Report from Great Britain for Application No. GB1303101.8 dated Aug. 12, 2013.
Yang eta!. "Novel method of forming human embryoid bodies in a polystyrene dish surface-coated with a temperature-responsive methylcellulose hydrogel", Biomacromol; vol. 8, pp. 2746-2752 (2007), See entire document, especially Results and Discussion.

* cited by examiner

*Primary Examiner* — Susan M Hanley
(74) *Attorney, Agent, or Firm* — Burns & Levinson, LLP; Shawn P. Foley

(57) ABSTRACT

The present invention relates to a medium for storing, preserving, culturing, and/or differentiating stem cells. The medium employs a synthetic thermo-responsive copolymer, dispersed in an aqueous vehicle, which allows the medium to be readily "switched" between a non-gelatinous (fluid) form and a gelatinous form by simply adjusting temperature across the gelling temperature of the medium. As such, stem cells can be easily captured within a 3D gel matrix by simply mixing the stem cells with the non-gelatinous/fluid form of the medium and then gelling the medium by adjusting the temperature across the gelling temperature of the medium. The stem cells encapsulated within the gelatinous form of the medium may then be preserved for a significant time period before either using the stem cells directly within the medium (e.g. in therapy, or in culturing, differentiation, and such like), or after their extraction from the medium.

29 Claims, 16 Drawing Sheets

MEDIA FOR STEM CELLS

CROSS REFERENCE TO RELATED APPLICATIONS

The present application is a national phase entry under 35 U.S.C. § 371 of International Application No. PCT/GB2014/050541, filed Feb. 21, 2014, published in English, which claims priority from GB 1303101.8, filed Feb. 21, 2013, all of which are incorporated herein by reference.

INTRODUCTION

The present invention relates to a medium for storing, preserving, culturing, and/or differentiating stem cells. The invention also relates to methods of storing, preserving, culturing, and/or differentiating stem cells using the media of the invention, as well as kits for forming the media of the invention, and compositions (e.g. pharmaceutical compositions) comprising stem cells dispersed in the media of the invention.

BACKGROUND

Stem cells have been the focus of intense research for many years. There is inherent interest in the biology and function of stem cells as well as significant interest in their potential therapeutic uses.

In the medical field, researchers believe that stem cells have the potential to revolutionize the treatment of certain human diseases. Indeed, a number of adult stem cell therapies already exist, such as bone marrow transplants that are used in the treatment of leukemia. In the future, medical researchers anticipate being able to use technologies derived from stem cell research to treat a wide range of diseases including cancer, Parkinson's disease, spinal cord injuries, Amyotrophic lateral sclerosis, multiple sclerosis, and muscle damage, amongst a number of other impairments and conditions.

For ongoing stem cell research and the development of stem cell-based therapies in the future, there is need for efficacious and cost-effective ways of culturing stem cells. In particular, there is a need for culture media that can maintain the viability and phenotype of stem cells during storage, transport and culturing. There is also a need for a stem cell culture medium which can be: (i) easily sterilized; (ii) eliminates or minimizes the presence of biological material; and (iii) permits the stem cells to be easily collected and isolated from the culture medium when desired.

Current stem cell media products on the market use animal-derived materials, which are sub-optimal due to the batch-to-batch variability in their composition.

The objective of the present invention is therefore to provide a medium for stem cells which addresses some or all of the aforementioned requirements.

BRIEF SUMMARY OF THE INVENTION

According to a first aspect of the present invention, there is provided a medium for stem cells, the medium comprising particles of a synthetic thermo-responsive copolymer dispersed in an aqueous vehicle;
wherein the medium is capable of undergoing a change between a non-gelatinous form and a gelatinous form in response to a change in temperature and, in the non-gelatinous form, the medium comprises a colloidally stable aqueous dispersion of the particles of the synthetic thermo-responsive copolymer and, in the gelatinous form, the medium is in the form of a gel that provides a scaffold or matrix capable of accommodating stem cells;
and wherein the aqueous vehicle further comprises nutrients for maintaining the viability of stem cells.

According to a second aspect of the present invention, there is provided a stem cell composition comprising one or more stem cells dispersed within a medium according to the first aspect of the invention.

According to a third aspect of the present invention, there is provided a method of producing a stem cell composition according to the second aspect of the invention, the method comprising:
(i) contacting a non-gelatinous form of the medium according to the first aspect of the invention with one or more stem cells to produce a fluid stem cell composition (i.e. a fluid dispersion of stem cells in the medium); and
(ii) optionally changing the temperature of the medium to cause the medium to change from the non-gelatinous form to the gelatinous form to thereby produce a gelled stem cell composition in which the stem cells are dispersed within the gelled medium.

According to a fourth aspect of the present invention, there is provided a method of storing or preserving one or more stem cells, the method comprising:
(i) contacting a non-gelatinous form of the medium according to the first aspect of the invention with one or more stem cells to produce a fluid stem cell composition;
(ii) changing the temperature of the medium to cause the medium to change from the non-gelatinous form to the gelatinous form and thereby produce a gelled stem cell composition; and
(iii) storing the gelled stem cell composition.

According to a fifth aspect of the present invention, there is provided a method of culturing stem cells, the method comprising:
(i) contacting a non-gelatinous form of the medium according to the first aspect of the invention with one or more stem cells to produce a fluid stem cell composition;
(ii) changing the temperature of the medium to cause the medium to change from the non-gelatinous form to the gelatinous form and thereby produce a gelled stem cell composition; and
(iii) culturing the stem cells within the gelled stem cell composition.

According to a sixth aspect of the present invention, there is provided a method of differentiating stem cells, the method comprising:
(i) contacting a non-gelatinous form of the medium according to the first aspect of the invention with one or more stem cells to produce a fluid stem cell composition;
(ii) changing the temperature of the medium to cause the media to change from the non-gelatinous form to the gelatinous form and thereby produce a gelled stem cell composition; and
(iii) culturing the stem cells under conditions to promote the differentiation of the stem cells.

According to a seventh aspect of the present invention, there is provided a method of releasing one or more stem cells from a gelled stem cell composition as defined herein, the method comprising:
(i) providing a gelled stem cell composition comprising one or more stem cells dispersed within a gelatinous form of the medium according to the first aspect;

(ii) changing the temperature of the stem cell medium to cause the medium to change from the gelatinous form to the non-gelatinous form to thereby produce a fluid stem cell composition; and (iii) optionally thereafter isolating said stem cells from the fluid stem cell composition.

According to an eighth aspect of the present invention, there is provided a method of making a medium according to the first aspect of the invention, the method comprising dispersing said particles of a synthetic thermo-responsive copolymer in an aqueous vehicle which further comprises nutrients for maintaining the viability of stem cells.

According to a ninth aspect of the present invention, there is provided a kit for preparing a medium according to the first aspect of the present invention, the kit comprising:

(i) particles of a synthetic thermo-responsive copolymer, as defined herein; and (ii) an aqueous vehicle which further comprises nutrients for maintaining the viability of stem cells.

According to a tenth aspect of the present invention, there is provided a pharmaceutical composition comprising a stem cell composition according to the second aspect of the invention and optionally one or more pharmaceutically acceptable excipients.

According to an eleventh aspect of the present invention, there is provided a pharmaceutical composition according to the tenth aspect for use in therapy.

According to an eleventh aspect of the present invention, there is provided a pharmaceutical composition according to the tenth aspect for use in stem cell therapy.

According to a twelfth aspect of the present invention, there is provided a use of medium as defined herein for the storage, preservation, culturing, and/or differentiation of one or more stem cells.

It will be understood to those skilled in the art that features, including optional, suitable, and preferred features of any particular aspect of the present invention may, unless stated otherwise, apply as features, including optional, suitable, and preferred features of any other aspect of the present invention.

BRIEF DESCRIPTION OF THE DRAWINGS

Embodiments of the invention are further described hereinafter with reference to the accompanying drawings, in which.

DETAILED DESCRIPTION OF THE INVENTION

Definitions

Figure 1:
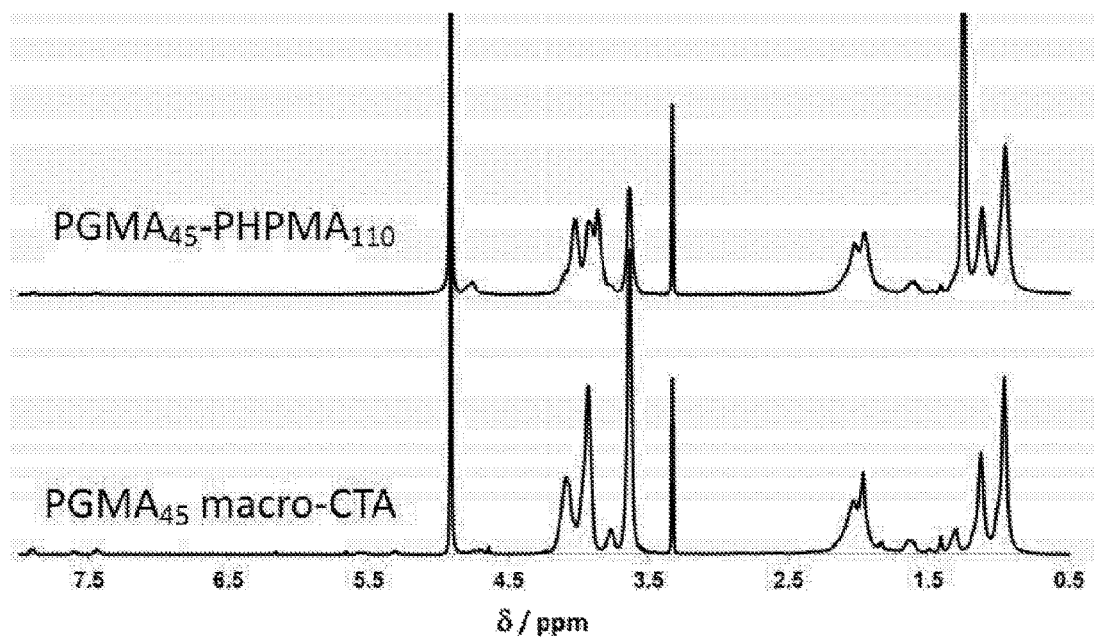
FIG. 1 is a $^1$H NMR spectrum recorded in $d_4$-methanol for $PGMA_{45}$-$PHPMA_{110}$ and $PGMA_{45}$.

Unless specifically stated to the contrary, all temperatures, temperature ranges, and any features/properties of materials corresponding to said temperatures, are given on the presumption of a prevailing atmospheric pressure of 1 bar.

Herein, the term "stem cell(s)" refers to cells which can divide and differentiate into a wide range of specialized cell types, and can also self-renew/replicate to yield more stem cells in their undifferentiated state. Though stem cells can now be artificially grown, mammalian stem cells include "embryonic stem cells", isolated from the inner cell mass of blastocysts, and "adult stem cells", which are found in various tissues, including:
 bone marrow, which requires extraction by drilling into bone (e.g. femur or iliac crest);
 adipose tissue (lipid cells), which requires extraction by liposuction;
 blood, which requires extraction through pheresis, wherein blood is extracted from the donor, passed through a machine that extracts the stem cells and returns other portions of the blood to the donor; and
 umbilical cord blood just after birth.

Herein, "stem cells" includes totipotent and pluripotent stem cells (which can mature to any cell type), but also multipotent or unipotent progenitor cells (which are more limited in terms of the cell types they can become). Most suitably, the "stem cells" for use with the present invention include totipotent and/or pluripotent stem cells, especially pluripotent stem cells.

Herein, the term "totipotent" refers to stem cells which can differentiate into embryonic and extra-embryonic cell types, and may lead to the construction of a complete viable organism. Such cells are produced by fusing an egg and sperm cell, and are further produced by the first few cycles of division of a fertilized egg.

Herein, the term "pluripotent" refers to stem cells that have descended from totipotent stem cells, and which can differentiate into substantially all cell types from any of the three germ layers, namely endoderm (interior stomach lining, gastrointestinal tract, lungs), mesoderm (muscle, bone, blood, urogenital), or ectoderm (epidermal tissues and nervous system). Though pluripotent cells can lead to any fetal or adult cell type, they cannot develop into a fetal or adult organism per se because they lack the ability to contribute to extra-embryonic tissue (e.g. placenta). Pluripotent stem cells (such as blastomeres) can be obtained from the inner cell mass (ICM) of mammalian embryos.

Herein, the term "multipotent" or "multipotent progenitor cell(s)" refers to stem cells that can still differentiate into a number of cell types, but only those of a closely related family. As such, multipotent cells have a more defined destiny that either totipotent or pluripotent stem cells. Multipotent progenitor cells can self-renew for long periods of time, but not indefinitely, unlike pluripotent stem cells. Multipotent progenitor cells have also been termed "adult stem cells" or "mesenchymal stromal cells" to denote cells that are present in tissue of a non-embryonic organism. Multipotent progenitor cells may be obtained, for example, from bone marrow, umbilical cord blood, peripheral blood, breast, liver, skin, gastrointestinal tract, placenta, and uterus. Multipotent progenitor cells may include neuronal stem cells capable of differentiating into neuronal cells, hematopoietic stem cells capable of differentiating into blood cells, mesenchymal stem cells capable of differentiating into bone, cartilage, fat, and muscle, and hepatic stem cells capable of differentiating into hepatocytes.

Herein, the term "differentiated cell" refers to a cell destined to become a specific cell type and usually not capable of differentiating into other cell types. Examples of differentiated cells include, for example, endothelial cells, smooth muscle cells, striated muscles, skin and interstitial fibroblasts, neuronal cells (e.g. astrocytes, neurons, and oligodendrocytes), cardiac cells, hepatic cells and pancreatic cells.

Herein, "undifferentiated cells" are stem cells that have not yet become a specific cell type.

Herein, references to "post-differentiated stem cells" means stem cells that have been differentiated in accordance with the present invention, i.e. using the stem cell media described herein, and unless stated otherwise are not intended to include stem cells that have been differentiated by any other method.

Herein, differentiated cells and multipotent progenitor cells include those derived from any animal, whether a human, monkey, pig, horse, cow, sheep, dog, cat, mouse, or rat, preferably those derived from humans.

Herein, the term "aqueous vehicle" refers to the medium throughout which the synthetic thermo-responsive copolymer is dispersed to form the medium of the invention. The aqueous vehicle necessarily includes nutrients which prolong the viability of stem cells stored therein. As such, the aqueous vehicle may simply allow stem cells to survive. However, the aqueous vehicle may be or may comprise a culture medium to facilitate growth (i.e. replication) and survival of the stem cells. Furthermore, the aqueous vehicle may be, may comprise, or may be have added thereto growth factors of other differentiating agents to facilitate in situ differentiation of the stem cells.

Herein, the term "culture medium", especially "standard culture medium", refers to a medium enabling the growth and survival of mammalian cells in vitro. A culture medium for use in the invention may include all of the pertinent media typically used in the art. The culture medium may be a cell culture minimum medium (CCMM), which generally comprises a carbon source, a nitrogen source and trace elements. Examples of a CCMM include, but are not limited to, DMEM (Dulbecco's Modified Eagle's Medium), MEM (Minimal Essential Medium), BME (Basal Medium Eagle), RPMI1640, F-10, F-12, alpha MEM (alpha Minimal Essential Medium), GMEM (Glasgow's Minimal Essential Medium), and IMDM (Iscove's Modified Dulbecco's Medium). A culture medium for use in the invention may further contain one or more of a number of different additives, as is known in the art, for example, an antibiotic, such as penicillin, streptomycin, gentamicin or combinations thereof, amino acids, vitamins, fetal calf serum or a substitute thereof.

Herein, the term "cultured" in reference to cells means a cell population that has been grown in the presence of defined culture medium under controlled environmental conditions, typically in an environment maintained at 37° C., and containing about 21% oxygen and about 5-10% $CO_2$ for mammalian cells. Similarly, the term "culturing" refers to the process of producing an enlarged population of cells by growth of a cell or cells of interest under controlled environmental conditions, typically in an incubator maintained at a set temperature and providing defined concentrations of oxygen and $CO_2$, and optionally other parameters such as humidity, and agitation in a controlled manner at a set rate.

Herein, the term "viable" when used in relation to cells, refers to living cells.

Herein, the term "cell viability" relates to the proportion of living cells in a given sample, which may be quantitatively assessed by methods well known in the art.

Herein, terms such as "preserved viability", "extended viability", "prolonged viability", "extended storage life", "prolonged maintenance" and "prolonged survival", are used interchangeably, and refer to the greater proportion of living cells that survives in a cell population that has been subject to one of the treatment methods of the invention (e.g. method of storage/preservation) as compared to a cell population or sample thereof which has not been so treated.

Herein, the term "room temperature" refers to temperatures in the range of 20 to 26° C.

Herein, the term "ambient temperature" refers to temperatures within the range of about 18° C. to about 32° C.

The temperature below which or above which the stem cell medium becomes or starts to become gelatinous is referred to herein as the "gelling temperature". Herein, to adjust the temperature "across" the gelling temperature means to either lower the temperature below the gelling temperature (in embodiments where the medium become gelatinous upon lowering the temperature from a certain point) or raise the temperature above the gelling temperature (in embodiments where the medium becomes gelatinous upon raising the temperature from a certain point).

Herein, the term "gelatinous" is used to describe a gel (i.e. jelly-like) form of a substance (e.g. a stem cell medium). Though a gel may be hard or soft, typically gel forms of the media of the present invention are soft. Such gels are non-fluid, and typically do not flow in their steady state.

Herein, the term "non-gelatinous" is used to describe a (substantially) fluid form of a substance, such as a stem cell medium. Such fluid forms generally exhibit flowable properties.

General Description

The present invention essentially provides a medium for stem cells (i.e. a stem cell medium) which is capable of undergoing reversible gelation. The medium can therefore be readily "switched" between a non-gelatinous (fluid) form and a gelatinous form by simply adjusting temperature across the gelling temperature of the medium. As such, stem cells can be easily captured within a 3D gel matrix by simply mixing the stem cells with the non-gelatinous/fluid form of the medium and then gelling the medium by adjusting the temperature across the gelling temperature of the medium. The stem cells encapsulated within the gelatinous form of the medium may then be preserved for a significant time period before either using the stem cells directly within the medium (e.g. in therapy, or in culturing, differentiation, and such like), or after their extraction from the medium.

In addition, the gelled medium may be used as a medium for 3D culturing and/or differentiation of the stem cells. The nutrients within the medium may be modified to promote the culturing of stem cells. Additional nutrients, growth factors or incubation conditions may be used to promote stem cell differentiation. As such, the media of the present invention are extremely versatile.

Since the media of the invention can be adapted for relatively long-term storage of stem cells at ambient or room temperature, a more convenient, cost-effective, and energy-efficient stem cell storage system is provided. In particular, the media of the invention can alleviate the need for expensive cooling systems for the long-term storage and/or transportation of stem cells.

The materials used to produce the media of the present invention are relatively inexpensive, and can be readily produced using robust and scalable synthetic chemistry techniques.

Given that the media of the invention are entirely synthetic, there is no risk of biological contamination of, or interference with, the stem cells being stored (unlike when animal-derived products are used to form such media). Moreover, the synthetic nature of the media of the present invention facilitates much better batch-to-batch reproducibility and thereby reduces the undesirable variability commonly associated with the use of biologically-derived products, such as animal proteins. The synthetic nature of the copolymer of the invention also allows for judicious tuning of the media to optimize the properties as required.

The media of the invention are biocompatible with and non-toxic towards stem cells. The relative softness and permeability of the gelatinous form of the media enables nutrients to easily diffuse throughout the media to ensure that stem cells contained therein are suitably nourished and thereby preserved.

The media of the invention are easy to sterilize, since the non-gelatinous forms thereof can be easily sterilized by filtration (due to the small size of the thermo-responsive copolymer particles and the fluid nature of the medium in this form).

In preferred embodiments, the media of the invention are also transparent, which enables stem cells to be studied, for example, using an optical microscope, within the media itself. This is particularly useful when the media are also being used for culturing and/or differentiating the stem cells in question.

The switchable form of the media enables facile transfer of stem cells between receptacles, and may also facilitate accurate volumetric measurement and dispensing of stem cells.

The reversible gelation of the media of the invention enables facile manipulation of the stem cells stored therein, since they can be stored for a time within the gelatinous form of the media before being released into the non-gelatinous fluid form to enable receipt of additional nutrients before the stem cells are recaptured within the gelatinous form of the media.

The media of the invention are also biocompatible, so the media may itself serve as a pharmaceutical carrier or vehicle for the therapeutic administration of stem cells, whether as part of an implant, patch, or other suitable administrable form of the stem cells. Moreover, the media may be tuned so that the gelling temperature is appropriate for whichever therapeutic use is envisaged.

A number of other advantages of the media of the invention will be apparent from the description that follows.

The Medium

The present invention provides a medium for stem cells, the medium comprising particles of a synthetic thermo-responsive copolymer dispersed in an aqueous vehicle;

wherein the medium is capable of undergoing a change between a non-gelatinous form and a gelatinous form in response to a change in temperature and, in the non-gelatinous form, the medium comprises a colloidally stable aqueous dispersion of the particles of the synthetic thermo-responsive copolymer and, in the gelatinous form, the medium provides a scaffold or matrix that is capable of accommodating stem cells;

and wherein the aqueous vehicle further comprises nutrients for maintaining the viability of stem cells.

Suitably, the medium is a stem cell medium.

The medium is suitably thermo-responsive due to the presence of the synthetic thermo-responsive copolymer particles.

The medium is suitably capable of undergoing a reversible change between a non-gelatinous form and a gelatinous form in response to a change in temperature. This means that at least one cycle of reversible gelation can be carried out, i.e. at least one cycle of gelation and subsequent degelation (i.e. fluidization) may be selectively induced (by an appropriate temperature change). In a particular embodiment, the medium is capable of reversible gelation over more than one cycle, and suitably the reversible gelation is retained over multiple cycles of gelation and degelation. Such reversible gelation allows stem cells to be repeatedly captured/encapsulated within and then released from the gelled stem cell compositions of the invention.

The transition between the non-gelatinous form and the gelatinous form, and vice versa, of the medium is suitably characterized by a phase transition or change of state of the medium. The phase transition is suitably due to a temperature-dependent change in the morphology of the thermo-responsive copolymer particles. On the macroscopic scale, the phase transition of the medium is characterized by a change in the viscosity of the medium. The non-gelatinous form of the medium is a relatively free-flowing fluid and thus has a relatively low viscosity, whereas the gelatinous form is a substantially free-standing gel, which is not free-flowing and thus has a relatively high viscosity.

The gelatinous form of the medium is suitably relatively soft gel.

In preferred embodiments, the medium exists in the non-gelatinous form at temperatures below the gelling temperature and in a gelatinous form at temperatures above the gelling temperature of the medium.

In preferred embodiments, the medium is in the gelatinous form at ambient temperature and/or at room temperature. Suitably, the medium is in the gelatinous form at temperatures greater than or equal to 15° C., suitably greater than or equal to 20° C., suitably greater than or equal to 30° C. Suitably, the medium is in the gelatinous form at temperatures between 35 and 40° C. Suitably, the medium remains in a gelatinous form at temperatures up to 45° C., suitably up to 60° C.

In preferred embodiments, the medium is in the non-gelatinous form at temperatures less than or equal to 10° C., suitably less than or equal to 5° C. Suitably, the medium remains in a non-gelatinous form at temperatures down to 0° C., suitably down to −5° C.

Suitably, the "gelling temperature" of the stem cell medium is between 5 and 30° C., suitably between 10 and 25° C., suitably between 15 and 20° C. The gelling temperature and properties of the medium can be varied by adjusting certain key parameters, such as the degree of polymerization of the thermo-responsive copolymer or parts thereof, the hydrophilic/hydrophobic balance of the thermo-responsive copolymer, the particular monomers present in the thermo-responsive copolymer, etc. As such, the present invention provides a means to tune the gelling temperature of the medium for the particular application concerned.

The medium is suitably biocompatible. In particular, the medium itself is suitably non-toxic to cells, especially non-toxic to stem cells. Suitably, storing stem cells within the medium will preserve the viability of said stem cells where appropriate nutrients are present.

The medium is suitably biocompatible with mammalian cells, especially human cells (e.g. when incorporated within compositions, such as pharmaceutical compositions, for therapeutic applications), and is suitably non-toxic to mammalian species and/or cells in the therapeutically effective quantities. This allows the medium to serve as a vehicle or pharmaceutical carrier for administering stem cell therapies (or differentiated cell therapies that are derived from stem cells).

The medium is suitably transparent in the gelatinous form, or at least sufficiently transparent to allow any cells captured within the gelatinous medium to be observed with the naked eye and/or by appropriate magnification (e.g. using an optical or confocal microscope). The medium may suitably be transparent in the non-gelatinous form, or at least sufficiently transparent to allow any cells dispersed therein to be visible with the naked eye and/or by appropriate magnification (e.g. using an optical or confocal microscope). Such transparency allows for in situ analysis of cells within the medium.

The medium (excluding any stem cells/post-differentiated cells) is suitably free from animal-derived products. Suitably, the medium of the present invention is free from any thermo-responsive proteins, peptides or other biopolymers obtained from biological (e.g. animal) sources. For example, the thermo-responsive copolymer is suitably completely synthetic. The synthetic nature of the thermo-responsive copolymers used within the medium allows batch-to-batch variation to be minimized (in contrast the media which employ organism-derived thermo-responsive copolymers) and thereby improves the reliability of the stem cell media of the present invention.

In the gel form, the medium provides a 3D scaffold or matrix which is particularly suitable for storing, preserving, culturing, and/or differentiating stem cells. Suitably, the scaffold effectively mimics a three-dimensional (3D) extracellular matrix (ECM) found in vivo.

The medium of the present invention is suitably configured to permit selective capture or encapsulation of the stem cells in the gelatinous form of the medium. The stem cells can then be subsequently released and isolated by converting the medium back to the non-gelatinous form. For example, stem cells may be suitably encapsulated within the gelatinous medium by first mixing said stem cells with the non-gelatinous form of the medium and then causing the medium to change into its gelatinous form by adjusting the temperature across the gelling temperature, thereby encapsulating the stem cells within the gelatinous form of the medium. This provides a gelled stem cell composition. The stem cells may then be stored, preserved, cultured, and/or differentiated within the gelled stem cell composition. The stem cells may be suitably released from the gelled stem cell composition/matrix by causing the medium to change into its non-gelatinous form, again by adjusting the temperature across the gelling temperature. Optionally, the stem cells may then be recaptured within the gelatinous medium by repeating the whole process.

When the stem cells are released from the gelatinous form of the medium (e.g. by causing the stem cell medium to change into its non-gelatinous form) they may be suitably extracted from the non-gelatinous form of the medium by methods well known in the art, such as ultrafiltration and/or centrifugation.

It has been found that the processes outlined above do not affect the viability of the stem cells. The medium of the present invention is therefore a useful means for storing/preserving, culturing, and/or differentiating stem cells, and offers significant benefits to researchers, manufacturers, therapists, and clinicians who use stem cells.

The medium of the present invention suitably comprises between 1 and 30% w/w synthetic thermo-responsive copolymer, suitably between 2 and 20% w/w synthetic thermo-responsive copolymer, suitably between 3 and 12% w/w synthetic thermo-responsive copolymer. In a particular embodiment, the medium of the present invention comprises between 3 and 7% w/w synthetic thermo-responsive copolymer. In a particular embodiment, the medium of the present invention comprises between 8 and 12% w/w synthetic thermo-responsive copolymer. In a particular embodiment, the medium of the present invention comprises between 5 and 12% w/w synthetic thermo-responsive copolymer.

The medium of the present invention comprises nutrients for maintaining the viability of stem cells. Such nutrients may be added directly to the synthetic thermo-responsive copolymer or dispersion thereof so as to dilute the synthetic thermo-responsive copolymer. Alternatively, such nutrients may be introduced to a dispersion of the synthetic thermo-responsive copolymer via dialysis. Alternatively, such nutrients may be introduced to the medium via a combination of dialysis methods and direct addition.

Suitably, the stem cell medium is (substantially) free of surfactant, suitably comprising less than or equal to 1 wt % surfactant, suitably less than or equal to 0.5 wt % surfactants, suitably less than or equal to 0.1 wt % surfactant, suitably comprising zero surfactant.

Suitably, the stem cell medium is (substantially) free of sodium dodecyl sulphate (i.e. a type of surfactant sometimes used in RAFT polymerisation reactions), suitably comprising less than or equal to 1 wt % sodium dodecyl sulphate, suitably less than or equal to 0.5 wt % sodium dodecyl sulphate, suitably less than or equal to 0.1 wt % sodium dodecyl sulphate, suitably comprising zero sodium dodecyl sulphate.

Particles of Synthetic Thermo-Responsive Copolymer

The synthetic thermo-responsive copolymer is suitably synthetic, i.e. it is formed via synthetic chemical techniques rather than being biologically-derived.

The thermo-responsive copolymer is suitably biocompatible, and suitably non-toxic to stem cells. Suitably, the thermo-responsive copolymer is (substantially) free of surfactants. Suitably, the thermo-responsive copolymer is (substantially) free of sodium dodecyl sulphate The thermo-responsive copolymer suitably forms micellar particles within the aqueous vehicle. These particles suitably undergo a temperature-dependent change in morphology and it is this change in morphology that is understood to cause the medium to change from a non-gelled to a gelled state. Suitably the core-forming chains (i.e. $P_2$), which are suitably (substantially) aqueous/water insoluble or suitably otherwise hydrophobic (at least relative to the stabilizer chains (i.e. $P_1$)), are thermo-responsive. Suitably the stabilizer chains (i.e. $P_1$), which are suitably (substantially) aqueous/water soluble or suitably otherwise hydrophilic (at least relative to the core-forming chains (i.e. $P_2$)), are less thermo-responsive than the core-forming chains (i.e. $P_2$) and most suitably the stabilizer chains are (substantially) non-thermo-responsive. Suitably, therefore, it is the core-forming chains that are responsible for the thermo-responsive behavior of the copolymer. This is suitably achieved by forming the particles of thermo-responsive copolymer by starting with a pre-formed aqueously soluble polymer including moieties of Formula A (see below—this relates to the $P_1$ portion) and building upon said polymer a further (substantially) aqueously/water insoluble block ($P_2$) through chain extension via a RAFT polymerization in the presence of a (substantially) aqueously/water soluble monomer $M_2$ (since this facilitates optimal particle formation). Judiciously modifying the relative solubilities of the respective comonomers and polymers can facilitate the formation of thermo-responsive copolymers of this nature. It is straightforward for those skilled in the art to discern whether or not an individual polymeric block is aqueously/water soluble and/or thermoresponsive.

The temperature at which the particles undergo a change in morphology corresponds to the gelling temperature of the medium. Thus, in some embodiments, the change in morphology occurs between 15 and 30° C., suitably between 10 and 30° C., suitably between 6 and 36° C.

In the "non-gelatinous form" of the medium, the particles of thermo-responsive copolymer are a colloidally stable dispersion of polymeric particles. Suitably, the particles are nanoparticles that are less than 500 nm in size, and more suitably less than 100 nm. Suitably, the particles are of a substantially spherical shape (e.g. spheres or sphere-like particles), suitably in the form of micelles. This non-gelatinous form is naturally more fluid and less viscous than the corresponding gelatinous form of the stem cell medium. The non-gelatinous form of the medium is free-flowing and suitable for mixing stem cells therein.

In the "gelatinous form" of the medium, the particles of thermo-responsive copolymer are suitably colloidally stable polymeric particles having a different morphology to the particles present in the non-gelatinous form. Suitably, in the "gelatinous form" of the medium, the particles of thermo-responsive copolymer are suitably anisotropic "worms" or "worm-like" particles. These elongated particles interact with each other to form the gelatinous form of the medium. Without wishing to be bound by any particular theory, it is believed that these "worm-like" particles interact with one another and this interaction is believed to give rise to the "gelatinous form" of the medium. The gelatinous form of the stem cell medium is suitably relatively soft, albeit not free-flowing, which facilitates diffusion of the nutrients and helps to accommodate living stem cells and thereby prolong their viability. The elastic modulus (G') is typically 20-1000 Pa, suitably 10-200 Pa.

The shape of such particles may be duly verified using appropriate electron microscopy techniques (e.g. SEM, TEM) known in the art.

The thermo-responsive copolymer suitably has a number-average molar mass ($M_n$) between 1,000 g/mol and 100,000 g/mol, suitably between 5,000 g/mol and 80,000 g/mol, more suitably between 7,000 g/mol and 70,000 g/mol, most suitably between 10,000 g/mol and 60,000 g/mol.

The thermo-responsive copolymer suitably has a number-average molar mass ($M_n$) and weight-average molar mass ($M_w$) such that $M_w/M_n$ is between 1.05 and 1.50.

The nature of the particles of the thermo-responsive copolymer, whether within the gelatinous or non-gelatinous form of the stem cell medium, depends on the present temperature (i.e. which determines the copolymer morphology) and the nature of the copolymer itself (i.e. whether it forms "spherical" particles or "worm-like" particles at the temperature in question).

The thermo-responsive copolymer is suitably an amphiphilic copolymer (i.e. comprises both hydrophilic and hydrophobic properties). In many embodiments, the thermo-responsive copolymer comprises at least one hydrophilic polymeric block and at least one hydrophobic polymeric block.

Suitably the thermo-responsive copolymer comprises a thermo-responsive polymeric block. In a particular embodiment, the thermo-responsive copolymer comprises a thermo-responsive polymeric block and a non-thermo-responsive block, wherein the non-thermo-responsive polymeric block is suitably (substantially) not thermo-responsive in a temperature range between 0° C. and 45° C. In a particular embodiment, the thermo-responsive copolymer comprises a first polymeric block that is thermo-responsive, and a second polymeric block that is less thermo-responsive than the first polymeric block.

In certain embodiments, the thermo-responsive copolymer may be defined by

 Formula B

Formula B wherein $P_1$ represents a polymeric component derived from a monomer $M_1$ and $P_2$ represents a substantially aqueously insoluble polymeric component derived from an aqueously soluble monomer $M_2$, $P_1$, $M_1$, $P_2$, and $M_2$ may be defined by any of the meanings given thereto in WO 2011/110841 A2 (UNIVERSITY OF SHEFFIELD, filed 8 Mar. 2011) to the extent that this affords a thermo-responsive copolymer in accordance with the present invention (i.e. non-thermo-responsive copolymers are duly excluded). Likewise, a thermo-responsive copolymer defined by Formula B may be produced by any of the methods defined in WO 2011/110841 A2 (UNIVERSITY OF SHEFFIELD, filed 8 Mar. 2011), to the extent that this affords a thermo-responsive copolymer in accordance with the present invention (i.e. non-thermo-responsive copolymers are duly excluded). As such, WO 2011/110841 A2 is incorporated herein by reference. The required thermo-responsive properties can be duly verified by dispersing the copolymer within water or even an aqueous vehicle in accordance with the invention and examining the resulting dispersion over a range of temperatures for a transition between a "non-gelatinous" and "gelatinous" form or vice versa.

Suitably, $P_1$ is at least partially aqueously/water-soluble. Suitably, $P_1$ is (substantially) aqueously/water-soluble. Suitably $P_1$ is more aqueously/water-soluble than $P_2$.

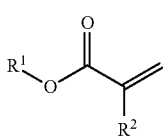

Formula $M_{1A}$

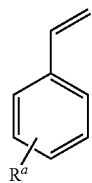

Formula $M_{1B}$

Suitably, each monomer $M_1$ is selected from a monomer of the Formula $M_{1A}$, $M_{1B}$ and/or $M_{1C}$:

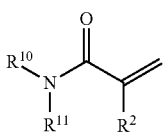

Formula $M_{1C}$ where $R^1$, $R^{10}$ and $R^{11}$ represents a substituent of $M_{1A}$ or $M_{1C}$ which allows $P_1$ to be at least partially aqueously soluble,
$R^2$ represents H, $CH_3$ or CN,
$R^S$ represents one or more substituents of the aromatic ring effective to allow $P_1$ to be least partially aqueously soluble, and
each monomer $M_2$ is selected from a monomer of the Formulae $M_{2A}$ and/or $M_{2B}$:

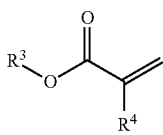

Formula $M_{2A}$

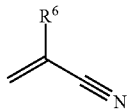

Formula $M_{2B}$ where $R^3$ is a substituent of $M_2$ which allows $P_2$ to be substantially aqueously insoluble, and $R^4$ and $R^6$ independently represent H or methyl;
or $P_1$ is a copolymer comprising a monomer $M_1$ with a monomer $M_2$ provided that the polymer $P_1$ remains aqueously soluble.

In an embodiment of the invention, $P_1$ is a copolymer, which comprises two or more monomers $M_1$ of the Formulae $M_{1A}$, $M_{1B}$ and $M_{1C}$ defined above.

In an alternative embodiment, $P_1$ is a homopolymer comprising a single monomer $M_1$ selected from the monomers of Formulae $M_{1A}$, $M_{1B}$ and $M_{1C}$ defined above.

In an embodiment, $P_1$ is a homopolymer or copolymer comprising monomers of formulae $M_{1A}$ or $M_{1B}$.

In an embodiment, $P_1$ is a homopolymer or copolymer comprising monomers of Formulae $M_{1A}$.

In an embodiment, $P_1$ is a copolymer comprising a monomer $M_1$ with a monomer $M_{2A}$ provided that the polymer $P_1$ remains aqueously soluble.

In a further embodiment of the invention, $P_2$ is a copolymer, wherein monomer $M_2$ is selected from two or more monomers of the Formulae $M_{2A}$ and $M_{2B}$ defined above.

In an alternative embodiment, $P_2$ is a homopolymer comprising a single monomer $M_2$ selected from the monomers of Formulae $M_{2A}$ and $M_{2B}$.

Suitably, $P_2$ is a polymer or copolymer comprising monomers $M_2$ selected from the monomers of Formulae $M_{2A}$. Thus, in a particular embodiment, $P_2$ is a polymer or copolymer comprising monomers of Formula $M_{2A}$.

In certain embodiments, $P_2$ may additionally comprise a cross-linking monomeric unit (such as, for example, EGDMA), whether $P_2$ is a copolymer or a homopolymer. In other embodiments, $P_2$ does not comprise any cross-linking monomeric units.

In a preferred embodiment of the invention, both of $P_1$ and $P_2$ are homopolymers as defined above.

In an embodiment, the thermo-responsive copolymer is defined by Formula B, and $P_1$ is itself a polymer or copolymer comprising glycerol monomethacrylate (GMA) monomeric units, and $P_2$ is itself a polymer or copolymer comprising 2-hydroxypropyl methacrylate (HPMA) monomeric units. $P_1$ and/or $P_2$ may be homopolymers, for example poly(glycerol monomethacrylate) (PGMA) and poly(2-hydroxypropyl methacrylate) (PHPMA) respectively. Alternatively, either or both of $P_1$ and/or $P_2$ may be copolymers or else substantially homopolymers doped with other monomeric units. For example, whereas $P_1$ may be a homopolymeric poly(glycerol monomethacrylate) (PGMA) block, $P_2$ may be a copolymeric block comprising both GMA and HPMA monomeric units or $P_2$ may be a copolymeric block comprising both (diethylene glycol) methacrylate (DEGMA) and HPMA monomeric units.

In a particular embodiment, the thermo-responsive copolymer is a block copolymer of Formula B [$P_1$-$P_2$] selected from the group including:

1. PGMA-PHPMA. The PGMA block may suitably have a degree of polymerization (DP) between 10 and 200, suitably between 25 and 100, suitably between 30 and 80. The PHPMA block may suitably have a degree of polymerization (DP) between 50 and 300, suitably between 60 and 280, suitably between 70 and 250.

2. PGMA-P(GMA-HPMA). The PGMA block may suitably have a degree of polymerisation (DP) of 10 to 120. The P(GMA-HPMA) block may suitably have a degree of polymerisation (DP) of between 20 and 200, suitably between 50 and 150, suitably between 70 and 120. The ratio of GMA to HPMA monomer units within the P(GMA-HPMA) block is suitably between 10:1 and 1:10, suitably between 1:1 and 1:5, suitably between 1:2 and 1:3.

3. PGMA-P(DEGMA-HPMA). The PGMA block may suitably have a degree of polymerisation (DP) between 10 and 200, suitably between 30 and 100, suitably between 40 and 60. The P(DEGMA-HPMA) block may suitably have a degree of polymerisation (DP) between 20 and 200, suitably between 50 and 150, suitably between 70 and 120. The ratio of DEGMA to HPMA monomer units within the P(DEGMA-HPMA) block is suitably between 10:1 and 1:10, suitably between 1:1 and 1:5, suitably between 1:2 and 1:3.

Particles of the thermo-responsive copolymer are suitably pre-formed using a suitable synthetic process prior to their inclusion within a stem cell medium of the present invention. However, in certain embodiments, the particles of thermo-responsive copolymer may be formed in situ within an aqueous medium, which aqueous medium is or becomes (following the addition of appropriate nutrients) the aqueous vehicle of the stem cell medium. The particles may be initially formed in either their "gelatinous" or "non-gelatinous" form (e.g. as worms or spheres respectively), though it is often more convenient, from a handling point of view, to initially form the particles in their "non-gelatinous" form (i.e. colloidally dispersed fluid-like form) or at least to convert them to their "non-gelatinous" form prior to producing the stem cell medium.

In preferred embodiments, the particles of thermo-responsive copolymer are pre-formed and then ultra-filtered prior to their use within a stem cell medium. Most suitably said particles are ultra-filtered while in their "non-gelatinous" form (i.e. ultra-filtered as an aqueous dispersion of colloidally stable polymeric particles, preferably substantially "spherical" particles). Suitably such an ultra-filtration is performed at low temperature, suitably where the pre-filtered aqueous dispersion of colloidally stable copolymer particles is at a temperature of at or below 10° C., more suitably at or below 5° C., when it is ultra-filtered. The particles are suitably ultra-filtered in this manner to sterilize the particles prior to their inclusion within a stem cell medium. However, such ultra-filtration may also conveniently remove reagents and by-products involved in the formation of the particles. The particles are then suitably dispersed in the aqueous vehicle or within an aqueous medium, which is subsequently adapted to form the aqueous vehicle of the invention.

In particular embodiments of the invention, the particles of thermo-responsive copolymer are pre-formed by controlled synthetic polymerization methodologies, most preferably by polymerization-induced self-assembly (i.e. whereby particles are formed in situ within the aqueous polymerization reaction medium). In a particular embodiment, the particles of thermo-responsive copolymer are prepared using a Reversible Addition-Fragmentation chain Transfer (RAFT)-type polymerization process conducted under aqueous dispersion polymerization conditions. In especially preferred embodiments, the particles of thermo-responsive copolymer are produced by any of the methods defined in WO 2011/110841 A2 (UNIVERSITY OF SHEFFIELD, filed 8 Mar. 2011), to the extent that this affords a thermo-responsive copolymer in accordance with the present invention (i.e. non-thermo-responsive copolymers are duly excluded). Such techniques are ideal for producing colloidal particles of diblock copolymers in a controlled and reproducible manner. As such, WO 2011/110841 A2 is incorporated herein by reference. The required thermo-responsive properties can be duly verified by dispersing the copolymer within water or even an aqueous vehicle in accordance with the invention and examining the resulting dispersion over a range of temperatures for a transition between a "non-gelatinous" and "gelatinous" form or vice versa.

In a particular embodiment, the particles of thermo-responsive copolymer is formed by forming a block copolymer of Formula B as defined above in an aqueous-based medium by admixing:

(a) an aqueously soluble polymer including moieties of Formula A

Formula A where X represents a terminal group of $P_1$, at least some of the groups X being a chain transfer agent (CTA) terminal group, with (b) a monomer $M_2$ as defined above and initiating a reversible addition-fragmentation chain transfer (RAFT) polymerisation conducted under aqueous dispersion polymerization conditions, to provide the block copolymer of Formula B.

Suitably, the reversible addition-fragmentation chain transfer (RAFT) polymerization to form the block copolymer of Formula B is performed (substantially) in the absence of a surfactant. Suitably, the reversible addition-fragmentation chain transfer (RAFT) polymerization to form the block copolymer of Formula B is performed (substantially) in the absence of sodium dodecyl sulphate. Suitably the reversible addition-fragmentation chain transfer (RAFT) polymerization to form the block copolymer of Formula B is performed so that, if any surfactants are present, the weight ratio of total surfactant(s) to the aqueously soluble polymer including moieties of Formula A is 1:25 or less (i.e. less surfactant), suitably 1:100 or less, suitably 1:200 or less. Suitably the reversible addition-fragmentation chain transfer (RAFT) polymerization to form the block copolymer of Formula B is performed so that, if any surfactants are present, the weight ratio of total surfactant(s) to the monomer $M_2$ is 1:25 or less (i.e. less surfactant), suitably 1:100 or less, suitably 1:200 or less, suitably 1:1000 or less.

In a particular embodiment, the thermo-responsive copolymer is defined by Formula B:

Formula B wherein $P_1$ represents a substantially aqueously soluble (or water-soluble) polymeric component derived from a monomer $M_1$ (which is also suitably substantially aqueously/water soluble) and $P_2$ represents a substantially aqueously insoluble (or water-insoluble) polymeric component derived from an aqueously soluble (or water-soluble) monomer $M_2$;

wherein either:
i) the core-forming chains (i.e. $P_2$) are thermo-responsive and the stabilizer chains (i.e. $P_1$) non-thermo-responsive; or
ii) the stabilizer chains (i.e. $P_1$) are less thermo-responsive than the core-forming chains (i.e. $P_2$) and most suitably the stabilizer chains are (substantially) non-thermo-responsive.

As aforementioned, $P_1$, $M_1$, $P_2$, and $M_2$ may be defined by any of the meanings given thereto in WO 2011/110841 A2 (UNIVERSITY OF SHEFFIELD, filed 8 Mar. 2011) to the extent that this affords a thermo-responsive copolymer in accordance with the present invention (i.e. non-thermo-responsive copolymers are duly excluded).

Aqueous Vehicle

The aqueous vehicle comprises water and suitable nutrients for the stem cells. The aqueous vehicle suitably comprises 80-95 wt % water The nutrients may be any suitable cell culture nutrients known in the art.

The aqueous vehicle suitably comprises buffered saline, such as phosphate-buffered saline.

In an embodiment, the aqueous vehicle may be or may comprise an aqueous culture medium known in the art The aqueous vehicle suitably comprises, as nutrients, a stem cell culture medium, suitably a human stem cell culture medium, most suitably a human embryonic stem cell culture medium (e.g. KO-DMEM medium, from Invitrogen). Such stem cell culture media are suitably themselves provided as an aqueous solution or dispersion of the relevant nutrients. Suitably the aqueous vehicle comprises at least 20% w/w stem cell culture medium, suitably at least 40% w/w stem cell culture medium. Suitably the aqueous vehicle comprises at most 97% w/w stem culture medium, suitably at most 95% w/w stem culture medium, suitably at most 80% w/w stem cell culture medium, suitably at most 60% w/w stem culture medium.

The medium may further comprise growth factors or other nutrients that promote the differentiation of the stem cells into a desired cell type.

Stem Cells

Any stem cells may be used in the media of the present invention.

In certain embodiments, the stem cells for use with the methods and media of the present invention are mammalian stem cells, most suitably human stem cells. In a particular embodiment, the stem cells are embryonic stem cells (e.g. human embryonic stem cells). However, such embryonic stem cells are suitably stem cells other than those produced or obtained by a method involving the destruction of human embryos and/or human embryonic stem cells. In alternative embodiments, the stem cells are non-embryonic (e.g. adult) stem cells.

Suitably the stem cells are substantially undifferentiated. Suitably the stem cells are pluripotent stem cells.

Embryonic stem cells are suitably isolated from the inner cell mass of blastocysts.

Non-embryonic stem cells may be obtained and isolated from various tissues, including:
bone marrow, which requires extraction by drilling into bone (e.g. femur or iliac crest); adipose tissue (lipid cells), which requires extraction by liposuction;
blood, which requires extraction through pheresis, wherein blood is extracted from the donor, passed through a machine that extracts the stem cells and returns other portions of the blood to the donor;
umbilical cord blood just after birth.

The stem cells used in accordance with the present invention are suitably totipotent or pluripotent stem cells, most suitably pluripotent stem cells. Such, pluripotent stem cells can suitably differentiate into cell types from any of the three germ layers, namely endoderm (interior stomach lining, gastrointestinal tract, lungs), mesoderm (muscle, bone, blood, urogenital), or ectoderm (epidermal tissues and nervous system). Alternatively, the stem cells may be multipotent stem cells.

The stem cell medium of the present invention is suitably configured to capture/encapsulate the one or more stem cells within a gel matrix whilst the stem cell medium is in the gelatinous form. Such stem cells are suitably encapsulated within a 3D scaffold along with relevant nutrients which allow the stem cells to survive and even grow within the gel.

A suitable preparation of isolated cells may be one which is enriched for multipotent progenitor cells, typically obtained from a source such as bone marrow, whole peripheral blood, leukopheresis or apheresis products, umbilical cord blood and cell suspensions prepared from tissues or organs.

Multipotent progenitor cells may be isolated using methods of cell culture, expansion and separation known in the art, for example using fibrin microbeads as disclosed by the inventor of the present invention in U.S. Pat. Nos. 6,737,074; and 6,503,731. Alternative methods include those disclosed in U.S. Pat. Nos. 7,592,174; 5,908,782; 5,486,359, and U.S. Patent Application Publication Nos. 2010/0068191; 2009/0124007; and 2010/0297233 among others.

Typical methods for cell enrichment and/or isolation include density step gradients (e.g., Ficoll®, colloidal silica), elutriation, centrifugation, lysis of erythrocytes by hypotonic shock, and various combinations of such methods. For example, purification of stem cells from bone marrow requires removal of erythrocytes and granulocytes, which is often accomplished by Ficoll® density gradient centrifugation, followed by repeated washing steps by conventional centrifugation.

Methods for cell enrichment and/or isolation may also include filtration on various types of filters known in the art for cell separation. For example, tangential flow filtration, also known as cross-flow filtration, may be used for enriching stem cells from a heterogeneous mixture of bone marrow or blood constituents, as disclosed in U.S. Pat. No. 7,790,039.

Separation of multipotent cells from mixtures may also incorporate a step of absorption to a suitable substrate such as a plastic culture vessel.

Isolated multipotent progenitor cells for use in the invention include those termed "mesenchymal stem cells" (also referred to herein as "MSC"), such as those obtained from bone marrow stroma and umbilical cord blood, which have the ability to differentiate in vitro into different cell types, in particular chondrocytes, osteoblasts, adipocytes and myocytes. In vitro studies have demonstrated the capability of MSC to differentiate into muscle, neuronal-like precursors, cardiomyocytes and possibly other cell types. In addition, MSC have been disclosed to provide effective feeder layers for expansion of hematopoietic stem cells.

In a particular embodiment, the stem cells are pluripotent stem cells, especially pluripotent human embryonic stem cells. Stem cells are suitably harvested mechanically (e.g. via pipette) before transfer to the medium of the present invention. Suitably, stem cell aggregates are added to the stem cell medium. Suitably, the volume ratio of stem cells (or stem cell aggregates) to medium is between 1:1000 and 1:5, more suitably between 1:100 and 1:10, most suitably between 1:50 and 1:20. For example, about 20 μL of stem cell aggregates (typically each sized 20-200 μm) is added to about 600 μL of medium.

Accommodation of Stem Cells within the Medium

When in the gelatinous form, the medium is capable of accommodating live stem cells. Furthermore, the stem cells in the medium maintain their viability over prolonged periods and without any phenotypic change (unless agents or conditions to promote differentiation are present).

Suitably, the gelatinous medium is capable of maintaining the viability of stem cells for at least 7 days, suitably at least 14 days, more suitably at least 21 days, more suitably at least 28 days, most suitably at least 56 days. Assuming no differentiating agents (e.g. growth factors) are added to the medium, the accommodated stem cells are maintained in undifferentiated form, and remain viable. Such accommodated stem cells can suitably self-renew/replicate following extraction from the medium.

Suitably, the gelatinous form of the stem cell medium is capable of accommodating live stem cells at ambient temperature and/or optimal culturing (i.e. 30-42° C.) and/or differentiation temperatures, depending on whether the stem cells are being stored, cultured, and/or differentiated. Suitably, the gelatinous form of the stem cell medium is capable of accommodating live stem cells at temperatures between 15 and 42° C. Such stem cells may be stored in a dormant state or statis (i.e. where substantially no differentiation and/or proliferation takes place).

Method of Producing Stem Cell Medium

The present invention provides a method of making a medium according the first aspect of the invention, the method comprising dispersing said particles of a synthetic biocompatible thermo-responsive copolymer in an aqueous vehicle which further comprises nutrients for maintaining the viability of stem cells.

The particles of the thermo-responsive copolymer and the aqueous vehicle may be prepared/provided separately and then mixed together. The particles of the synthetic thermo-responsive copolymer are then dispersed within an aqueous vehicle, suitably at a temperature whereby the resulting medium exists in its non-gelatinous form.

The particles of thermo-responsive copolymer may be provided by any of the methods described herein, in particular via methods disclosed in WO 2011/110841 A2 (UNIVERSITY OF SHEFFIELD, filed 8 Mar. 2011). As such, said particles are suitably formed in situ in an aqueous medium by controlled radical polymerization, such as RAFT polymerization. Suitably, such particles are formed by:
(i) providing a pre-formed polymeric block (e.g. of PGMA) dissolved in a polymerization medium/solvent (e.g. water); and
(ii) growing from said pre-formed polymeric block a second polymeric block (e.g. by initiating further polymerization, e.g. RAFT polymerization, using appropriate monomer(s)), wherein said second polymeric block renders the resulting diblock copolymer (substantially) insoluble within the polymerization medium/solvent, and thereby forms colloidal particles in situ.

The particles of thermo-responsive copolymer are suitably sterilized prior to incorporation within the stem cell medium. Such sterilization may be performed through ultra-filtration. Most suitably the particles are ultra-filtered in their non-gelatinous form (i.e. when the relevant colloidal particles are smallest and hence the fluid viscosity is minimized). As such, the particles may be ultra-filtered at a suitable temperature that provides the particles (or corresponding dispersion thereof) in a non-gelatinous form.

Ultra-filtration of the particles of thermo-responsive copolymer may be suitably performed through a 0.01-1 μm filter, suitably a 0.3-0.6 μm filter. In some embodiments, the filter may be a 0.22 or a 0.45 μm filter.

Suitably, the aqueous vehicle into which the particles of thermo-responsive copolymer are to be dispersed is pre-formed separately prior to dispersing the particles of thermo-responsive copolymer therein. However, the aqueous vehicle may alternatively be prepared in situ, for example, after the particles have been initially dispersed in a partially formed aqueous vehicle (e.g. water). In such cases, the relevant nutrients may be added to the partially formed aqueous vehicle after the particles have been duly dispersed.

Once formed, the medium is suitably stored or used immediately with stem cells.

Stem Cell Compositions

The present invention provides a stem cell composition, comprising one or more stem cells dispersed within a stem cell medium as defined herein.

The aqueous vehicle, in particular the stem cell nutrients therein, may readily diffuse throughout the gelatinous form of the medium. Suitably, the ready diffusion of the aqueous vehicle and/or nutrients contained therein throughout the gelatinous form of the stem cell matrix allows the stem cells encapsulated therein to be stored, preserved, cultured, and/or differentiated, depending on the content of the stem cell medium and/or aqueous vehicle.

The stem cell composition matrix may comprise up to a 10% v/v stem cells. The stem cell matrix may comprise at least 0.5% v/v stem cells.

Method of Forming the Stem Cell Compositions

The present invention also provides a method of producing a stem cell composition according to the second aspect of the invention, the method comprising:
(i) contacting a non-gelatinous form of the medium according to the first aspect of the invention with one or more stem cells to produce a fluid stem cell composition (i.e. a fluid dispersion of stem cells in the medium); and
(ii) optionally changing the temperature of the medium to cause the medium to change from the non-gelatinous form to the gelatinous form to thereby produce a gelled stem cell composition in which the stem cells are dispersed within the gelled medium.

Suitably, prior to initiating gelation of the stem cell composition, the fluid stem cell composition is sufficiently agitated, suitably to provide a fluid stem cell composition having the one or more stem cells dispersed in a (substantially) homogeneous fashion.

Preferably, the stem cell composition is then gelled by causing the medium to change from a non-gelatinous form to a gelatinous form, and thereby produce a gelled stem cell composition.

Method of Storing and/or Preserving Stem Cells

The present invention provides a method of storing or preserving one or more stem cells, the method comprising:
(i) contacting a non-gelatinous form of the medium according to the first aspect of the invention with one or more stem cells to produce a fluid stem cell composition;
(ii) changing the temperature of the medium to cause the medium to change from the non-gelatinous form to the gelatinous form and thereby produce a gelled stem cell composition; and
(iii) storing the gelled stem cell composition.

In preferred embodiments, step (i) of the above methods is suitably performed with the stem cell medium at a temperature of at or below 10° C., suitably at or below 5° C.

Changing the temperature may involve increasing or decreasing the temperature respectively above or below the gelling temperature, depending on the gelling properties of the medium and the thermo-responsive copolymer associated therewith.

In preferred embodiments, the stem cell medium is non-gelatinous below the gelling temperature and gelatinous above the gelling temperature. As such, step (ii) of the above methods suitably involves raising the temperature of the stem cell composition, initially from below the gelling temperature, up to or above the gelling temperature. Most suitably, step (ii) involves adjusting the temperature of the stem cell matrix from at or below 10° C. up to or above 18° C., suitably up to or above 35° C., most suitably up to about 37° C.

The stem cells may then be stored within the gelled stem cell composition for a suitable period of time. In particular, the stem cells may be viably stored within the matrix for at least 7 days, suitably at least 14 days, suitably at least 21 days, suitably at least 28 days, suitably at least 56 days. However, a practitioner may choose to store said stem cells for less time. Suitably the stem cells are stored at a temperature at or above 18° C., suitably at or above 35° C., most suitably at about 37° C.

The gelled stem cell composition within which the stem cells are stored may itself be suitably contained, suitably within a container, most suitably within a sealed container. In some embodiments, the stem cell matrix is stored within a sealed atmosphere comprising at least 1% v/v $CO_2$, suitably at least 3% v/v $CO_2$, more suitably at least 4.5% v/v $CO_2$. Suitably the sealed atmosphere comprises no more than 8% $CO_2$, suitably no more than 6% $CO_2$. The sealed atmosphere suitably has at least 80% humidity, suitably at least 90% humidity, suitably about 95% humidity. The sealed atmosphere suitably has at most 100% humidity, suitably at most 98% humidity.

During storage of the stem cells within the medium of the invention, the gelled medium may be overlayed with a nutrient medium, such as a stem cell culture medium described herein, especially a human embryonic stem cell culture medium. Such a nutrient medium may be periodically replaced and/or replenished (e.g. at least every two days). Such a process may help to maintain viability of the stem cells.

In addition to capturing and storing the stem cells, the methods above may involve a subsequent step of releasing the stem cells. Typically this involves causing the medium to revert to its non-gelatinous form to give a fluid stem cell composition (e.g. by adjusting the temperature to at or below 100° C. or at or below 5° C.), and may further involve extracting the stem cells from this fluid stem cell composition. Stem cells may be extracted mechanically, for example, via pipette. Such stem cells may be extracted as aggregates, suitably in the same manner they are harvested prior to introduction to the media of the present invention. The stem cells may then be subsequently used in any appropriate manner.

The medium of the invention suitably retards and/or prevents stem cell differentiation and/or proliferation during storage within said medium (particularly as compared to storage in standard stem cell culture media), especially for storage periods of 21 days or less. Proliferation status or reduction can be adjudged via visual inspection, for instance, via a microscope. Differentiation status or reduction can be adjudged by inspection of cell morphology and via analysis by fluorescent activated cell sorting (FACS) with specific marker monoclonal antibodies.

Method of Culturing Stems Cells

The present invention provides a method of culturing stem cells, the method comprising:
(i) contacting a non-gelatinous form of the medium according to the first aspect of the invention with one or more stem cells to produce a fluid stem cell composition;
(ii) changing the temperature of the medium to cause the medium to change from the non-gelatinous form to the gelatinous form and thereby produce a gelled stem cell composition; and
(iii) culturing the stem cells within the gelled stem cell composition.

The gelled stem cell composition provides a 3D gel network for culturing the stem cells. This is distinct from standard 2D cell culturing methods.

In preferred embodiments, culturing is conducted with the stem cell matrix at a temperature between 30 and 45° C., preferably 35 to 40° C., most preferably 37° C.

The culture medium may be the aqueous vehicle itself. In some embodiments, the aqueous vehicle is initially prepared as a culture medium. In some embodiments, additional ingredients may be added to the aqueous vehicle to generate the culture medium, for example, following storage, preservation, or differentiation of the stem cells.

The culture medium may suitably comprise standard culture nutrients that promote growth of the stem cells. Such standard culture media may include a HES medium and mouse embryonic fibroblast feeder cells. Such culture media are suitably different from any stem cell nutrients/culture media used within the media of the invention during storage of stem cells.

The method of culturing stem cells is intended, herein, to include culturing of any post-differentiated stem cells.

The method of culturing may additionally involve storing and/or preserving, before or after the culturing.

As with the method of storing or preserving stem cells, this method of culturing stem cells may involve a subsequent step of releasing the stem cells. Typically this involves causing the stem cell medium to become non-gelatinous to form a fluid stem cell matrix, and may further involve extracting the stem cells from the fluid stem cell matrix. The stem cells may then be used in any appropriate manner, including in any of the applications described herein.

Method of Differentiating Stem Cells

The present invention provides a method of differentiating stem cells, the method comprising:
(i) contacting a non-gelatinous form of the medium according to the first aspect of the invention with one or more stem cells to produce a fluid stem cell composition;
(ii) changing the temperature of the medium to cause the media to change from the non-gelatinous form to the gelatinous form and thereby produce a gelled stem cell composition; and
(iii) culturing the stem cells under conditions to promote the differentiation of the stem cells.

In preferred embodiments, culturing is achieved with the stem cell matrix at a temperature between 30 and 45° C., preferably 35 to 40° C., most preferably 37° C.

Suitable agents to promote differentiation of the stem cells may be present in the medium from the outset or, alternatively, may be added to the gelled stem cell composition during culturing (for example, following storage, preservation, or even culturing of the stem cells).

The method may involve cell culturing either before after stem cell differentiation. In some embodiments, such differentiation and culturing may be conducted in situ, though suitably sequentially rather than simultaneously.

The method of differentiating may additionally involve storing and/or preserving the cells, before or after stem cell differentiation.

As with the method of storing or preserving stem cells, this method of differentiating stem cells may involve a subsequent step of releasing the stem cells. Typically this involves causing the stem cell medium to become non-gelatinous to form a fluid stem cell matrix, and may further involve extracting the stem cells from the fluid stem cell matrix. The stem cells may then be used in any appropriate manner, including in any of the applications described herein.

Kit for Storing, Preserving, Culturing, and/or Differentiating Stem Cells

The present invention provides a kit for preparing a medium according to the first aspect of the present invention, the kit comprising:
(i) particles of a synthetic thermo-responsive copolymer, as defined herein; and
(ii) an aqueous vehicle which optionally further comprises nutrients for maintaining the viability of stem cells.

The particles may be preformed within an aqueous vehicle (e.g. water) prior to mixing the aqueous vehicle. Alternatively, the copolymer may be provided as a solid which is dispersed in the aqueous vehicle whereby it spontaneously forms suitable colloidal particles.

Suitably, aqueous vehicle further comprises nutrients for the stem cells, but these could be added separately and form separate components of the kit in certain embodiments.

Cell Therapies and Pharmaceutical Compositions

The present invention further provides a pharmaceutical composition comprising a stem cell composition according to the second aspect of the invention and optionally one or more pharmaceutically acceptable excipients.

Any suitable pharmaceutical excipients known in the art may be used. It is envisaged that most pharmaceutical compositions of the invention will be injections, infusions or implants comprising the stem cell compositions of the present invention.

According to an eleventh aspect of the present invention, there is provided a pharmaceutical composition as defined herein for use in therapy.

According to an eleventh aspect of the present invention, there is provided a pharmaceutical composition as defined herein for use in stem cell therapy.

According to a twelfth aspect of the present invention, there is provided a use of medium as defined herein for the storage, preservation, culturing, and/or differentiation of one or more stem cells.

No untoward toxicological effects are expected when a cell or stem cell matrix as defined hereinbefore is administered at suitable dosage ranges.

An effective amount of a cell or stem cell composition of the present invention for use in therapy is an amount that is sufficient to symptomatically relieve the symptoms of the medical condition in question, to slow the progression of said medical condition, or to reduce the risk of symptoms getting worse in patients (e.g. humans) with the medical condition.

The size of the dose for therapeutic or prophylactic purposes of a cell or stem cell composition of the invention will naturally vary according to the nature and severity of the conditions, the age and sex of the animal or patient and the route of administration, according to well-known principles of medicine.

The therapy, for which the cells and stem cell compositions defined herein may be used, is most suitably cell therapy, particularly stem cell therapy. The subjects intended to receive such therapies are suitably human or animal subjects. The therapy may include treatments for cellular defects (e.g. tissue defects, cartilage defects, bone defects, bone diseases), osteoarthritis, osteoporosis, spinal cord injury, periodontal disease, myocardial infarction, cancer, Parkinson's disease, amyotrophic lateral sclerosis, multiple sclerosis, muscular degenerative disorder and muscle damage. The therapies may involve bone marrow transplants, for example, to treat leukemia. The cells and stem cell matrices of the invention may be used in the restoration, the reconstruction, and/or the replacement of tissues and/or organs.

The media of the present invention may also be used to maintain stem cells obtained from a patient during certain therapeutic procedures, such as the maintaining of stem cells obtained from the bone marrow of a patient during intensive cancer chemotherapy or radiotherapy procedures. The stem cells may then be re-introduced to the patient following the medical treatment.

EXAMPLES

Materials and Methods

All reagents were purchased from Sigma-Aldrich and were used as received, unless otherwise noted. GMA monomer was provided by GEO Specialty Chemicals (Hythe, UK) and HPMA monomer was purchased from Alfa-Aesar (Heysham, UK).

Molecular weight distributions were assessed by gel permeation chromatography (GPC) using DMF as eluent. The GPC set-up comprised two Polymer Laboratories PL gel 5 μm Mixed-C columns and one PL polar gel 5 μm guard column maintained at 60° C. in series with a Varian 390 LC refractive index detector. The DMF mobile phase contained 10 mM LiBr and the flow rate was 1.0 mL min$^{-1}$. Ten near-monodisperse poly(methyl methacrylate) standards ($M_p$=625-618,000 g mol$^{-1}$) were used for calibration. The number-average molecular weight ($M_n$) and $M_w/M_n$ were calculated from GPC curves using near-monodisperse poly (methyl methacrylate) calibration standards.

$^1$H NMR spectra were recorded in $d_4$-methanol using a Bruker AV1-400 MHz spectrometer.

Transmission electron microscopy (TEM) studies were conducted using a Philips CM 100 instrument operating at 100 kV equipped with a Gatan 1 k CCD camera. Carbon-coated copper grids were glow-discharged for 20-30 sec to create a hydrophilic surface. Grids were then immersed in aqueous block copolymer dispersions (0.5 w/w %) for 1 min and then immersed for 20 s in a uranyl formate solution (0.75% w/v) for negative staining. Each grid was then blotted with filter paper and dried using a vacuum hose.

Example 1: Synthesis of a poly(glycerol monomethacrylate)-poly(2-hydroxypropyl methacrylate) (PGMA-PHPMA) Worm Gel Via RAFT Aqueous Dispersion Polymerization in Phosphate-Buffered Saline Synthesis of Poly(Glycerol Monomethacrylate) Macro-CTA Using 2-Cyanopropyl Dithiobenzoate (CPDB)

CPDB (0.576 g, 80% purity, 0.00208 mol) and GMA (20.00 g, 125.0 mol, 60 eq.) were weighed into a 250 ml round-bottom flask and purged with $N_2$ for 20 min. ACVA (0.117 g, 0.416 mmol, [CPDB]/[ACVA]=5.0) was added and the flask degassed for a further 5 min. Degassed anhydrous ethanol (30 ml) was added and the flask was degassed for a further 5 min prior to immersion in an oil bath set at 70° C.

After 115 min, $^1$H NMR analysis of the crude product indicated 71% monomer conversion. The resulting PGMA macro-CTA was purified by reprecipitating twice into excess dichloromethane from methanol, then dissolved in water and freeze-dried overnight to yield a pink powder, which was judged to be >99% pure by $^1$H NMR spectroscopy.

The mean degree of polymerization determined by $^1$H NMR was 45 (see FIG. 1).

DMF GPC analysis (vs. PMMA standards): $M_n$=13,800 g mol$^{-1}$ $M_w/M_n$=1.13.

Synthesis of PGMA$_{45}$-PHPMA 110 Diblock Copolymer Worms

PGMA$_{45}$ (4.904 g, 0.63 mmol) and HPMA (10.0 g, 69.4 mmol) were weighed into a 50 ml round-bottom flask and purged with N$_2$ for 20 min. ACVA (59.0 mg, 0.21 mmol) was added and the flask was degassed for a further 5 min. Phosphate-buffered saline solution (59 ml) previously purged with N$_2$ for 30 min, was then added and the solution was degassed for a further 5 min prior to immersion of the flask in an oil bath set at 70° C. After 3 h, $^1$H NMR analysis of the crude product indicated >99% HPMA monomer conversion based on the disappearance of the vinyl signals between 5.5 and 6.5 ppm. The resulting diblock copolymer was dialyzed against phosphate-buffered saline solution overnight to produce a monomer-free 20% w/w copolymer dispersion, which formed a free-standing gel at room temperature. A dried copolymer sample was analyzed by $^1$H NMR and DMF GPC.

Diblock composition determined by $^1$H NMR spectroscopy is PGMA$_{45}$-PHPMA$_{110}$ (see FIG. 1).

DMF GPC analysis (vs. PMMA standards): Mn=31,600 g mol$^{-1}$, Mw/Mn=1.09.

Figure 2:
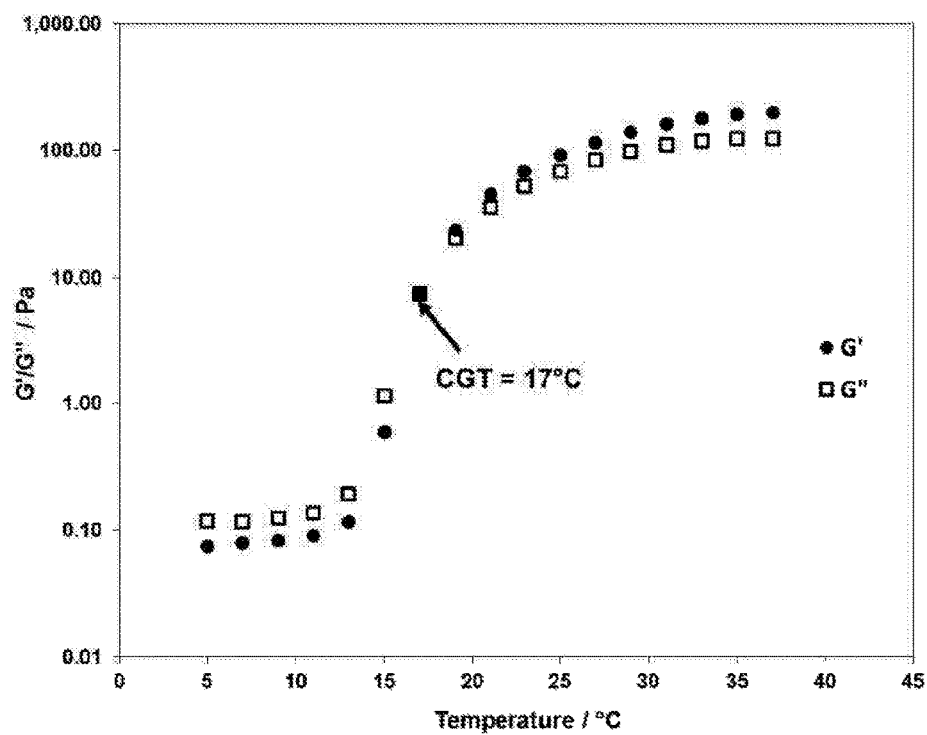
FIG. 2 shows the temperature dependence of the loss and storage moduli for a 10% w/w $PGMA_{45}$-$PHPMA_{110}$ diblock copolymer dispersion. The critical gelation temperature (CGT) was estimated to be 17° C.

Rheology measurements indicated a critical gelation temperature (CGT) of 17° C. (see FIG. 2).

Example 2: Synthesis of poly(glycerol monomethacrylate)-block-poly(2-hydroxypropyl methacrylate-stat-diethylene glycol methacrylate) (PGMA-P(HPMA-DEGMA)) Worm Gel Via RAFT Aqueous Dispersion Polymerization in Phosphate-Buffered Saline Synthesis of PGMA$_{55}$ Macro-CTA A PGMA macro-CTA was synthesized according to the above protocol. In this case, a GMA conversion of 88% was achieved after 2 h and a mean degree of polymerization (DP) of 55 was calculated via $^1$H NMR.

DMF GPC analysis (vs. PMMA standards): Mn=15,700 g mol$^{-1}$, Mw/Mn=1.17

Synthesis of PGMA$_{55}$-P(HPMA$_{84}$-Stat-DEGMA$_{36}$) Diblock Copolymer

Figure 3:
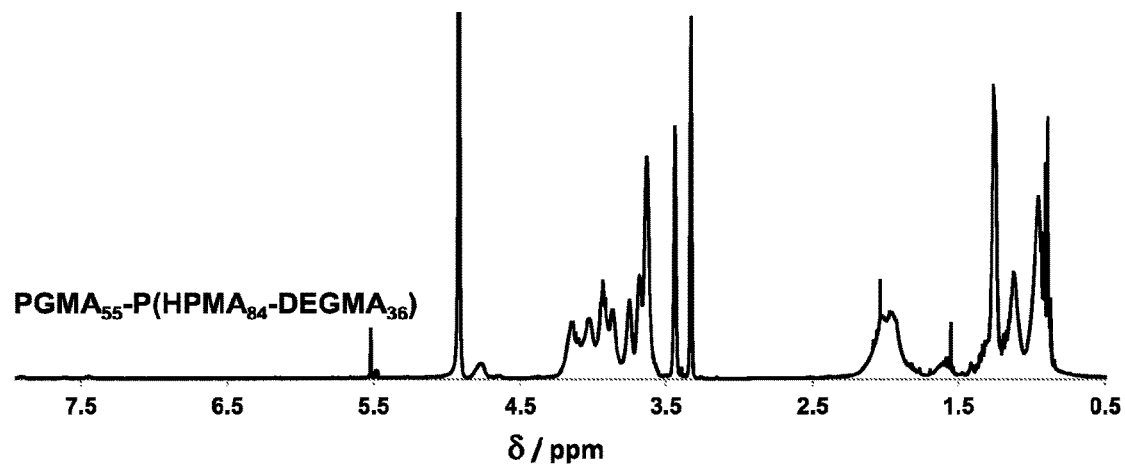
FIG. 3 is a $^1$H NMR spectrum recorded in $d_4$-methanol for crude $PGMA_{55}$-$P(HPMA_{84}$-stat-$DEGMA_{36})$.

PGMA$_{55}$ (0.750 g, 0.085 mmol), HPMA (1.028 g, 7.14 mmol), DEGMA (0.576 g, 3.06 mmol) and ACVA (8.0 mg, 0.028 mmol) were weighed into a 50 ml round-bottom flask. Phosphate-buffered saline solution (20 ml), previously purged with N$_2$ for 30 min, was added and the solution was purged with N$_2$ for a further 1 h prior to immersion of the flask in an oil bath set at 70° C. After 3 h, $^1$H NMR analysis of the crude product indicated >99% total monomer conversion based on the disappearance of the monomer vinyl signals between 5.5 and 6.5 ppm in the $^1$H NMR spectrum (see FIG. 3). The resulting diblock copolymer was dialyzed against phosphate-buffered saline solution overnight to produce a 10% w/w copolymer dispersion. A dry sample was analyzed by $^1$H NMR and DMF GPC.

Diblock composition determined by $^1$H NMR=PGMA$_{55}$-P(HPMA$_{84}$-stat-DEGMA$_{36}$)

DMF GPC analysis (vs. PMMA standards): $M_n$=36,000 g mol$^{-1}$, $M_w/M_n$=1.18

Figure 4:
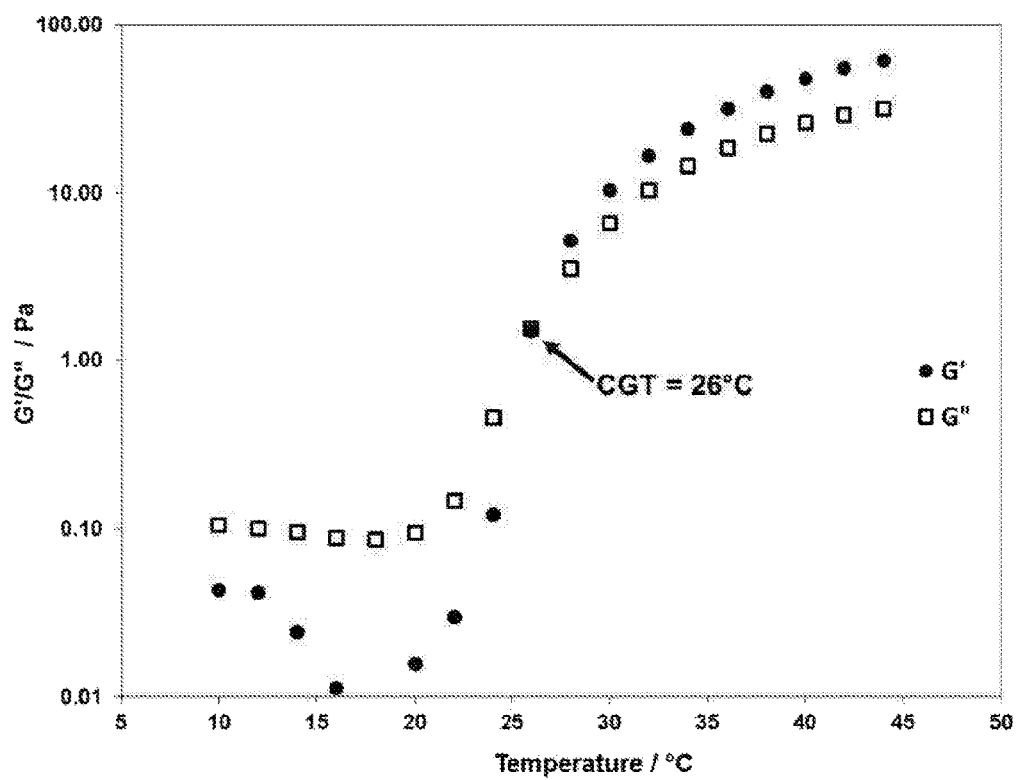
FIG. 4 shows temperature dependence of the loss and storage moduli for a 10% w/w $PGMA_{55}$-$P(HPMA_{84}$-stat-$DEGMA_{36})$ diblock copolymer. The critical gelation temperature (CGT) was estimated to be 26° C.

Rheology measurements indicated a critical gelation temperature of 26° C. (see FIG. 4).

Example 3: Production of a Gellable Stem Cell Medium 10 ml of a 10% w/w worm gel (in phosphate-buffered saline) derived from Example 1 was dialyzed for 24 h against 100 ml of human embryonic stem cell culture medium (KO-DMEM medium, Invitrogen) at 4° C. using pre-washed Spectra/Por dialysis membrane (molecular weight cut-off=1000) and then filter-sterilized using a 0.22 µm filter unit (Sartorius Minsart) previously cooled on ice. The gel mixture was diluted 50:50 with KO-DMEM medium (final 5% w/w) and pipetted into wells (600 µl/well) of a 12-well culture plate (Nunc) cooled on a bed of ice and the plate agitated to allow even spreading of the mixture.

The gellable stem cell media within the wells were then used in subsequent experiments.

Example 4: Capture, Storage, and Recovery of Stem Cells

Embryonic stem cells (Shef1, 11 and RPE1 cell lines) were harvested mechanically by pipette and 50-100 aggregates (50-100 µm diameter) transferred in a small volume (~20 µl) using a plastic Pasteur pipette to the gel wells described in Example 3 or to wells of a plate with cell culture medium alone (control). The plate was agitated to distribute the cell aggregates and immediately transferred to an incubator at 37° C. in 5% CO$_2$ in air and 95% humidity. After 5 min, the gel, which formed following a temperature-induced phase transition of the stem cell medium, was covered with 100 µl of cell culture medium and returned to the incubator. Medium overlaying the gel was replaced every 2 days and the wells examined by microscopy.

Stem cells were stored for 4, 7, 14, and 21 days prior to recovery and subsequent testing.

Example 5: Testing of Stored/Recovered Stem Cells

At 4, 7, 14 and 21 days, stem cell aggregates were recovered from well plates cooled on a bed of ice, at which point the stem cell media underwent a phase transition back to a fluid form and transferred to well plates with standard culture conditions (hES medium and mouse embryonic fibroblast feeder cells) to observe cell viability and spontaneous cell differentiation.

Figure 5:
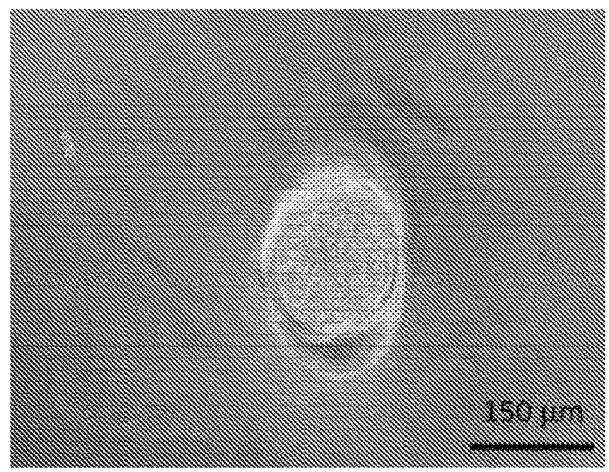
FIG. 5 shows an embryonic stem cell aggregate within a gel (after 4 days of culture). There was little expansion of the aggregate up to the end of the culture period.
Figure 6:
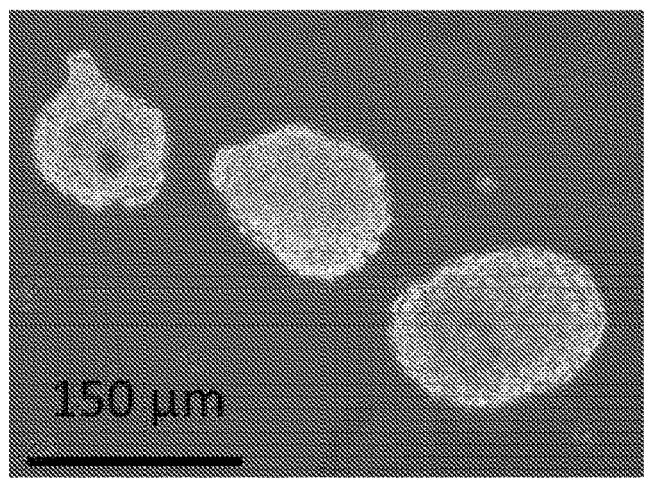
FIG. 6 shows embryonic stem cell aggregates recovered from a gel after 21 days. The aggregates show relatively little morphological indication of differentiation.
Figure 7:
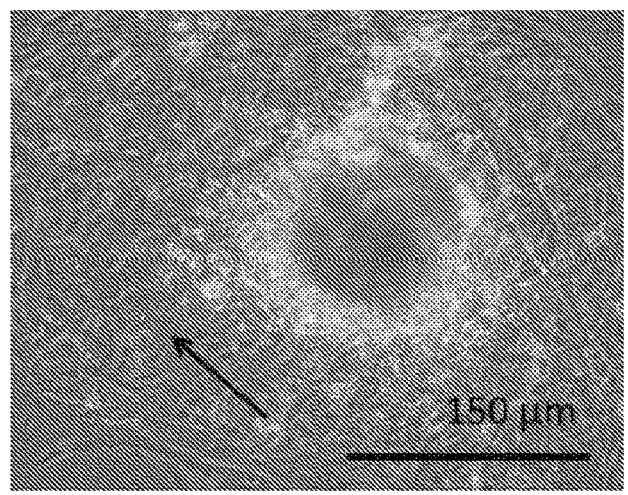
FIG. 7 shows an embryonic stem cell aggregate recovered from a gel after 21 days of culture and passaged into standard embryonic stem cell culture. After 48 h, a colony of embryonic stem cells is formed and spreads from the aggregate (arrowed).
Figure 8:
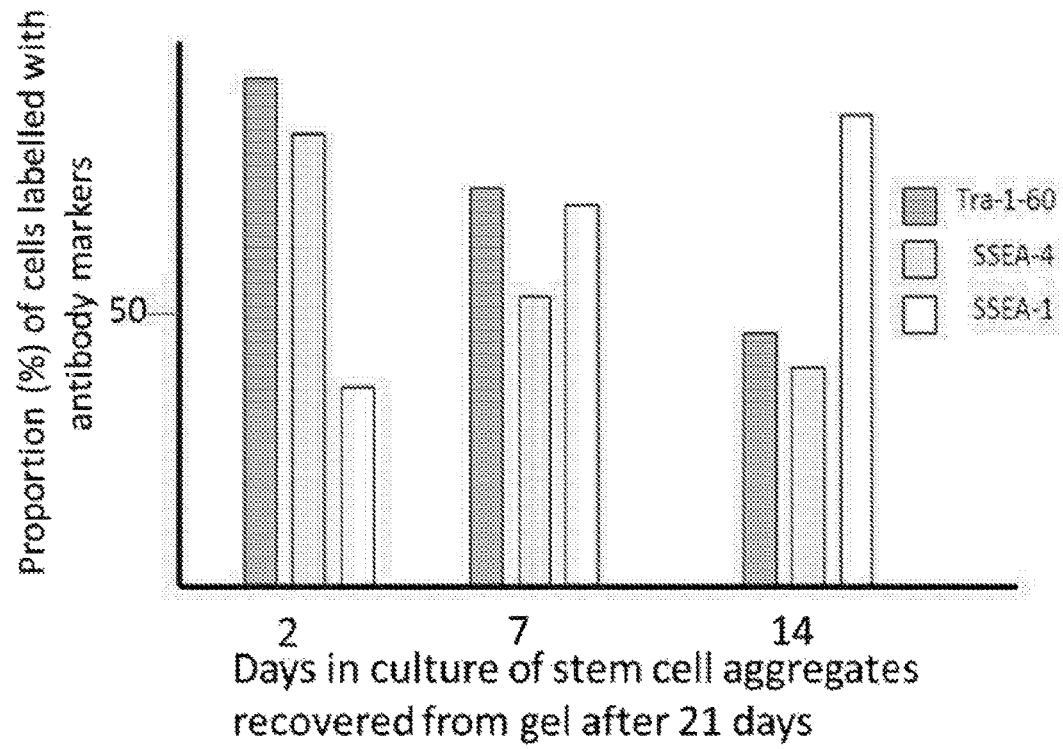
FIG. 8 shows a histogram of FACS analysis of the proportion of cells labeled with antibody surface markers Tra-1-60 (pluripotency), SSEA-4 (pluripotency), SSEA1 (differentiation) for embryonic stem cell aggregates previously incubated in a worm gel/cell composite medium for 21 days.
Figure 9:
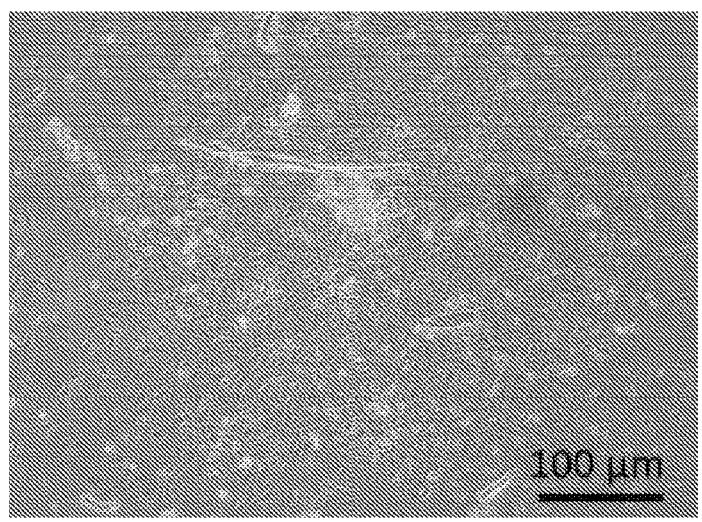
FIG. 9 shows an embryonic stem cell aggregate recovered from a gel after 21 days of culture and passaged into standard embryonic stem cell culture. After 14 days of culture, the aggregate shows morphological differentiation into various cell types.

It was possible to observe aggregates of stem cells enclosed in the gel with a small gap between the cells and the gel (see FIG. 5). As judged by phase-contrast microscope examination, there appeared to be little or no increase in the expansion of each cell aggregate with time in culture. When cell aggregates were recovered after the designated period of times above (FIG. 6), they showed viability as indicated by monolayer proliferation, and pluripotency by cellular differentiation indicated by cell morphology and analysis by fluorescent activated cell sorting (FACS) with specific marker monoclonal antibodies (FIGS. 7-9).

Figure 10:
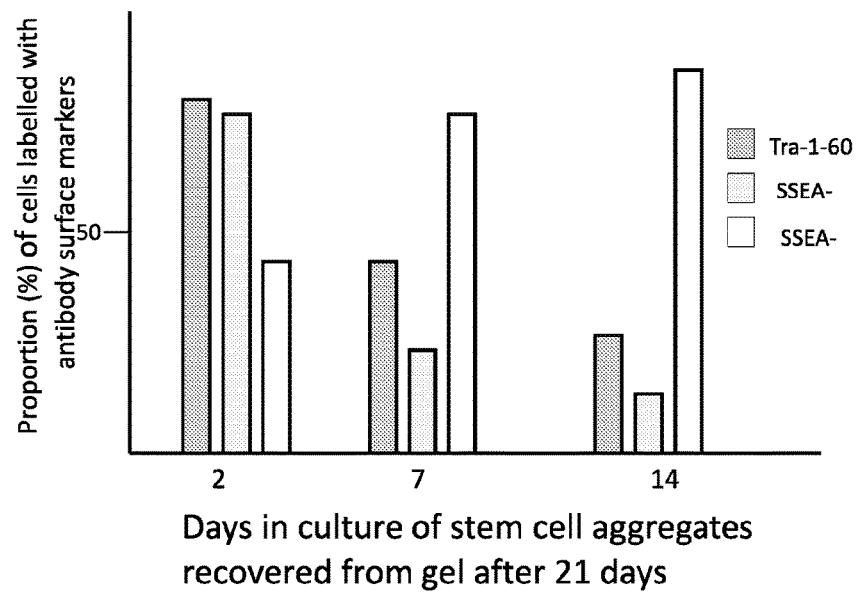
FIG. 10 shows a histogram of FACS analysis of the proportion of cells labeled with antibody surface markers Tra-1-60 (pluripotency), SSEA-4 (pluripotency), SSEA1 (differentiation) for embryonic stem cell aggregates plated to wells with medium alone (control—no gel).

The control stem cell aggregates plated to cell culture medium alone displayed immediate differentiation as indicated by morphological observation and FACS analysis (FIG. 10).

In summary, incubation of the embryonic stem cell aggregates in the gelled stem cell medium composition led to stasis of both stem cell differentiation and proliferation over 21 days as compared to standard stem cell culture.

Example 6: Encapsulation of NTERA2 Clone D1 Embryonic Carcinoma Stem Cells

This Example describes the use of 2-hydroxypropyl methacrylate (HPMA) copolymerized with poly(glycerol monomethacrylate) (PGMA), as a 3D scaffold for cell encapsulation. This copolymer can self-assemble into worm-like micelles at room temperature. These micelles are able to interact with each other so as to produce a 3D gel matrix. The evaluation of cell differentiation and pluripotency markers was assessed after encapsulation of NTERA2 clone D1 EC cells into the polymeric gel.

Experimental Procedures

The copolymer 3D worm gel was prepared as previously described by Armes et al (Adam Blanazs, Jeppe Madsen, Giuseppe Battaglia, Anthony J. Ryan, and Steven P. Armes *J. Am. Chem. Soc.* 2011, 133, 16581). The copolymer gel was then filter-sterilized using a 0.2 μm syringe filter. NTERA2 clone D1 embryonic carcinoma stem cells were detached and then encapsulated within the gel at 4° C. As a reference they were also plated in 2D into multiwell cell culture plates.

After 24 h, the cell culture media was replaced with the differentiating medium containing retinoic acid. The 3D (gel) and 2D (tissue culture plastic) systems were assayed for MTS and marker expression (e.g. TUJ1, TRA1-60 and Vin2Pb22) at different time points.

Results

Figure 11:
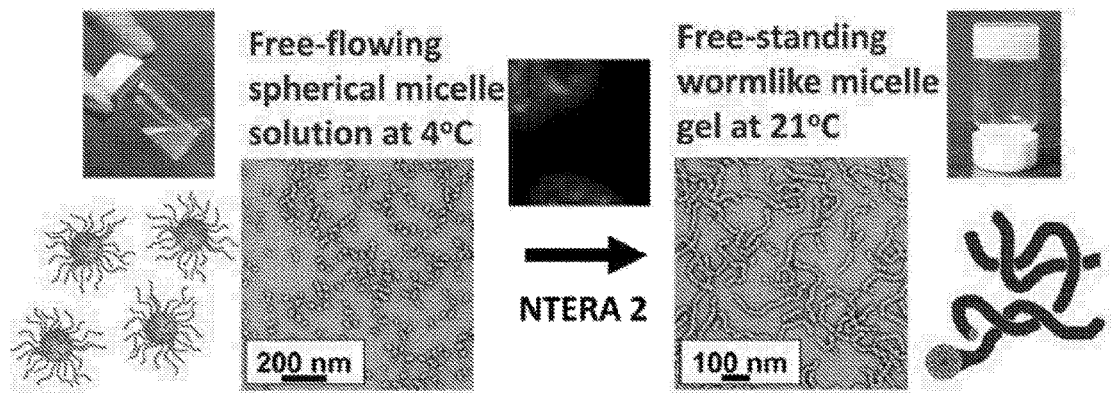
FIG. 11 shows a PGMA-HPMA block copolymer that forms different morphologies depending on the temperature.
Figure 12:
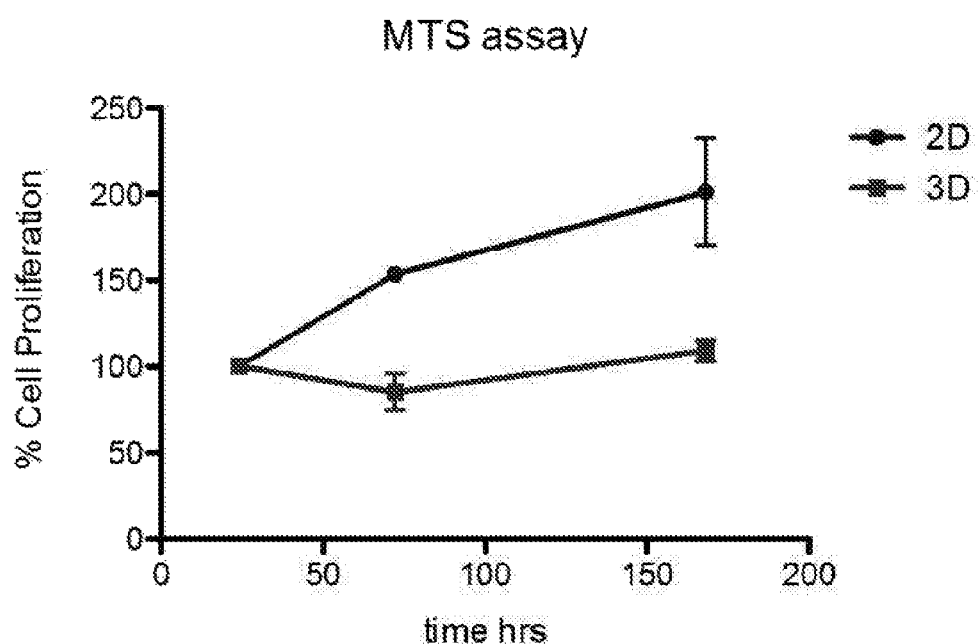
FIG. 12 shows an MTS assay. NTERA2 clone D1 cells were cultured up to 7 days in tissue culture plastic (2D) and in PGMA-PHPMA copolymer gels (3D).
Figure 13:
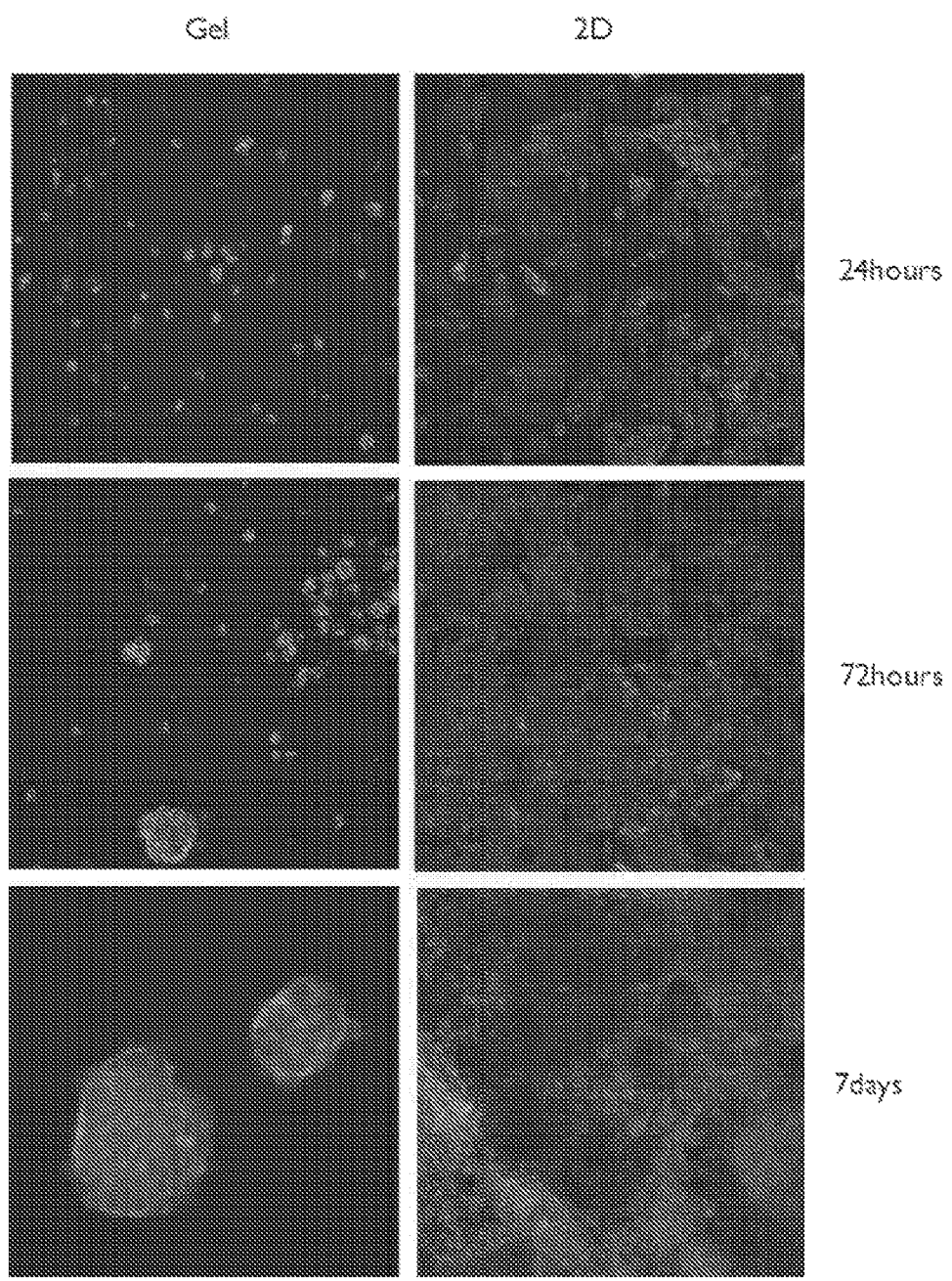
FIG. 13 shows Actin/DAPI staining of NTERA clone D1 EC cells. The comparison between the worm gel and a 2D planar substrate (tissue culture plastic) shows the proliferation of the cells up to 7 days.

After cells were encapsulated within gels (FIG. 11), they were kept in culture for seven days. The MTS assay (FIG. 12) showed that the worm gel is not toxic for this type of cell culture. Moreover, the actin-DAPI staining of the cells showed that they could divide, proliferate and form 3D spheroids after just 72 h (FIG. 13). After seven days, the spheroid formation became more evident with the formation of large cell colonies (FIG. 13).

Figure 14:
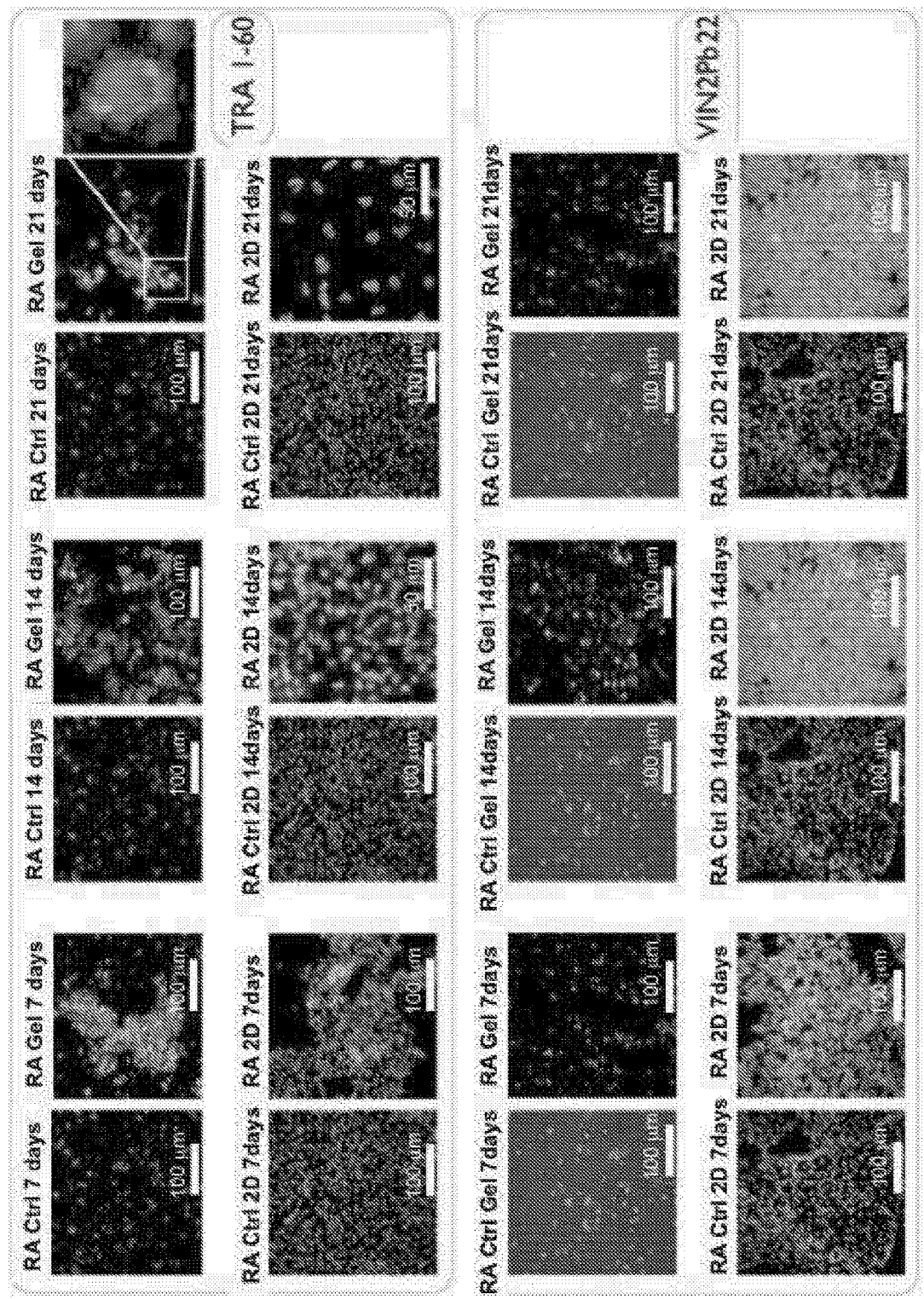
FIG. 14 shows marker expression analyzed by immunofluorescence. TRA 1-60 pluripotency marker expression (in red) and DAPI nucleic acid staining (in blue) after 7, 14, 21 days of culture of NTERA2 clone D1 EC cells with retinoic acid, in 3D (worm gel) and 2D (tissue culture plastic). Vin2Pb22 differentiation marker expression (in red) and DAPI nucleic acid staining (in blue) after 7, 14, 21 days of culture of NTERA2 clone D1 EC cells with retinoic acid, in 3D (worm gel) and 2D (tissue culture plastic).

TRA1-60, which is a well-known pluripotency stem cell marker, was used to stain the cells. FIG. 14 shows that, compared to the cells cultured on tissue culture plastic, encapsulated cells still expressed this marker after 14 and 21 days. Analysis of a differentiation marker such as Vin2Pb22 showed a singular situation where the expression was only detected in the 2D system (tissue culture plastic) up to 21 days.

Figure 15:
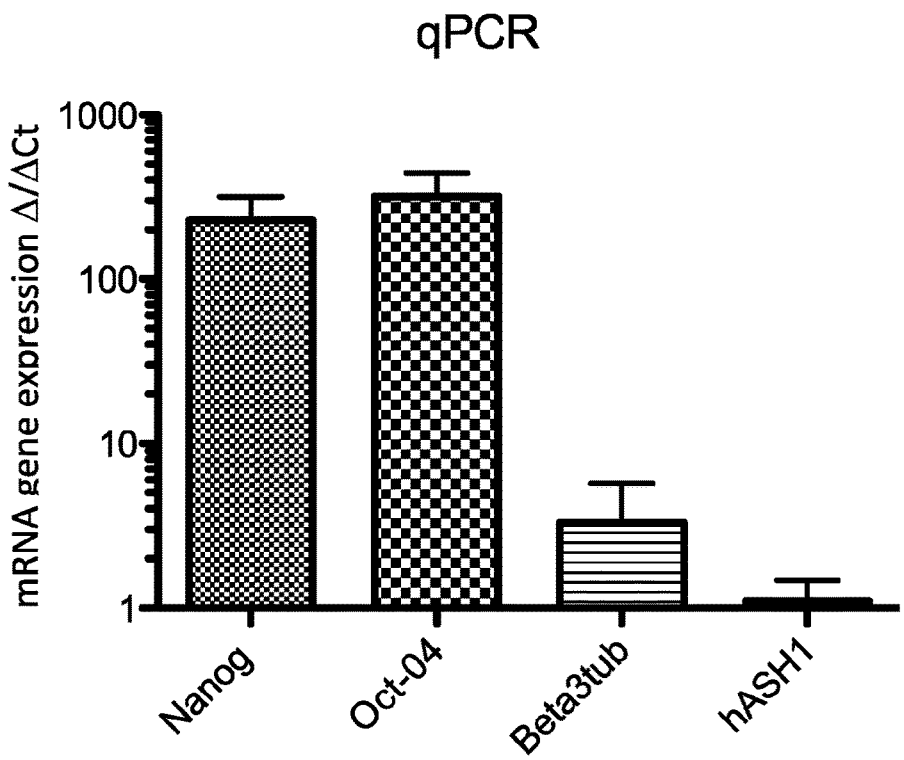
FIG. 15 shows marker expression analyzed by qPCR. Nanog, Oct-04 and Beta3Tubulin, h-ASH1 are, respectively, pluripotency and differentiation markers analyzed on NTERA2 clone D1 EC cells after 14 days of culture with retinoic acid. The values are expressed as $\Delta/\Delta$ Ct values.

The immunofluorescence assay data were confirmed by using qPCR to quantify the real difference in markers expression. FIG. 15 shows the expression of the two pluripotency markers Nanog and OCT-04, which differ significantly when compared to the differentiation markers Beta3 Tubulin and h-ASH1.

The results showed that the PGMA-PHPMA worm gel is not toxic for NTERA2 clone D1 EC cells. Moreover, the cells proliferated and formed spheroids as identified by Actin/DAPI staining. This makes the worm gels a good candidate for studying the differentiation process and cell development within a system that simulates a 3D cell environment. Study of the expressed markers suggest that the cells remain undifferentiated over 21 days of culture in retinoic acid. qPCR results confirmed that the cells do not differentiate with retinoic acid probably because of the low interactions with the PGMA-HPMA worm gel. These observations suggest that stem cell differentiation depends more mechano-transduction forces between cells and the scaffold than stimulation from bioactive molecules.

Example 7: Use of $PGMA_{55}$-$PHPMA_{135}$ Diblock Copolymer Worms to Prepare Worm Gels Directly in Cell Culture Media Synthesis of $PGMA_{55}$ Macro-CTA Using 2-Cyanopropyl Dithiobenzoate (CPDB)

CPDB (0.80 g, 3.6 mmol) and glycerol monomethacrylate (GMA, 40.59 g, 0.25 mol) were weighed into a 250 ml round-bottom flask and purged with $N_2$ for 20 min. ACVA (202.9 mg, 0.72 mmol) was added and the solution was degassed for a further 5 min. Degassed anhydrous ethanol (61 ml, 1.04 mol) was added and the solution was again degassed for a further 5 min prior to immersion in an oil bath set at 70° C. After 2 h, a $^1$H NMR spectrum recorded in $CD_3OD$ indicated approximately 80% GMA monomer conversion. The resulting polymer was purified by precipitating twice into excess dichloromethane from methanol to remove unreacted monomer. After the second precipitation, the purified polymer was filtered and the resulting solid was dissolved in water (200 mL). Residual dichloromethane was evaporated using a rotary evaporator set at 30° C. Once all traces of solvent were removed, the aqueous solution was freeze-dried overnight to afford a pink powder. $^1$H NMR spectroscopy studies of the pure polymer dissolved in $CD_3OD$ indicated a mean degree of polymerization of 55. DMF GPC analysis (vs. poly(methyl methacrylate) calibration standards) gave an $M_n$ of 14,100 g mol$^{-1}$ and an $M_w/M_n$ of 1.09.

Synthesis of $PGMA_{55}$-$PHPMA_{135}$ Diblock Copolymer Worms in 0.15 M PBS at 20% w/v Solids $PGMA_{55}$ (3.023 g, 0.33 mmol) and HPMA (6.240 g, 41.62 mmol) were weighed into a 100 ml round-bottom flask and purged with $N_2$ for 20 min. ACVA (31.1.0 mg, 0.11 mmol) was added and the flask was degassed for a further 5 min. Phosphate-buffered saline (PBS) solution (Dulbecco A, Oxoid, Basingstoke, 37 ml, 150 mM, previously purged with $N_2$ for 30 min.) was then added and the solution was degassed for a further 5 min prior to immersion of the reaction flask in an oil bath set at 70° C. for 2 h, after which $^1$H NMR spectra recorded in $CD_3OD$ indicated almost 100% HPMA conversion (disappearance of vinyl signals at 5.6 and 6.2 ppm). DMF GPC analysis (vs. poly(methyl methacrylate) calibration standards) gave an $M_n$ of 35,900 g mol- and an $M_w/M_n=1.10$ for the resulting $PGMA_{55}$-$PHPMA_{135}$ diblock copolymer.

For cell biology studies, three protocols were evaluated for purification and preparation of $PGMA_{55}$-$PHPMA_{135}$ worm gels, see below.

Protocol 1.

The as-synthesized 20% w/v aqueous $PGMA_{55}$-$PHPMA_{135}$ worm gel was dialyzed against PBS for 2 days at 4° C. with dialyzate (PBS) changes every 12 h (MWCO=1,000). The resulting cold free-flowing copolymer dispersion was diluted in the appropriate cell medium (DMEM, or Nutristem; pre-cooled to 4° C. prior to mixing) to the desired concentration (typically either 6% w/v or 10% w/v copolymer) and filter-sterilized at this temperature prior to use, as described below.

Protocol 2.

The as-synthesized 20% w/v $PGMA_{55}$-$PHPMA_{135}$ gel was dialyzed against PBS for 7 days at 4° C. with dialyzate changes every 12 h (MWCO=1,000). The resulting cold free-flowing dispersion was diluted in the appropriate cell medium (DMEM, or Nutristem; pre-cooled to 4° C. prior to mixing) to the desired concentration (typically either 6% w/v or 10% w/v copolymer) and filter-sterilized at this temperature prior to use, as described below.

Protocol 3.

The as-synthesized 20% w/v $PGMA_{55}$-$PHPMA_{135}$ gel was dialyzed against pure water for 7 days at 4° C. with dialyzate changes every 12 h (MWCO=1,000). The resulting gel was freeze-dried to yield a fine powder of dried copolymer worms. This powder was redispersed in the appropriate cell culture medium (DMEM, EB (Embryoid body medium), or Nutristem; pre-cooled to 4° C. prior to mixing) to afford either a 6% w/v or 10% w/v copolymer dispersion. The temperature was maintained at approximately 4° C. using an ice bath and magnetic stirring was continued for at least 20 min until full dispersion was achieved. The resulting liquid was filter-sterilized prior to use, as described below.

Sterilization Protocol

A 6% w/v $PGMA_{55}$-$PHPMA_{135}$ copolymer worm gel dispersed in the desired cell culture medium was cooled to 4° C. to induce the worm-to-sphere transition, and hence underwent degelation to afford a free-flowing dispersion of copolymer spheres. This cold low-viscosity fluid was then ultra-filtered using a sterile 0.20 μm syringe filter into a sterile vessel placed within a laminar flow cabinet. Syringes and filters were stored at −20° C. for at least 1 h prior to ultrafiltration to prevent gelation on contact. The resulting sterilized copolymer dispersion was then used immediately for cell colony encapsulation experiments, or stored at either 4° C. or −20° C. for future use (depending on the specifications of the cell medium).

Cell Viability in Direct Contact with $PGMA_{55}$-$PHPMA_{135}$ Worm Gels

Cell Viability Assays were Performed Using Primary Human Dermal Fibroblasts (HDFs).

Primary human dermal fibroblasts (HDF) were obtained in batches from the ATCC (LGC Standards, UK). They were predominantly extracted from breast reductions and neonatal foreskin. Fibroblasts were routinely cultured in T75 flasks using standard culture medium (DMEM supplemented with 10% FCS, $2 \times 10^{-3}$ mol $dm^{-3}$ L-glutamine, 0.625 μg/ml amphotericin B, 100 IU/ml penicillin and 100 μg/ml streptomycin). Fibroblasts were used for testing between passages 4 and 9.

Cell Viability Assays on Human Dermal Fibroblasts (HDFs) Using MTT Assay

HDFs were seeded in 24-well plates at a density of $3 \times 10^4$ cells per well and grown until 80% confluence (typically 48 h). Gels were evaluated both in direct contact with the cells and also in non-direct contact (basket method). A non-contact ThinCert (Greiner Bio-One, UK) set-up was used to identify any toxic low molecular weight compounds that might be present in the worm gels (e.g. unreacted HPMA monomer). ThinCert are small basket-like structures of tissue culture plastic with a polycarbonate membrane bottom that fits over a 24-well plate. Thus cells are exposed to the gel through the cell medium in the 24-well plates, but not by direct contact. This set-up discriminates between the effect of direct contact of the worm gel on the cells and the effect of residual small molecule impurities For the indirect contact set-up, 250 μl of the 10% copolymer gel was added to each ThinCer basket. Cells were placed below each basket and immersed in the appropriate cell culture medium (500 μl). For the direct contact set-up, the cell medium was removed from the wells and the gel (typically 500 μl) was applied directly onto the cell monolayers. Gel batches were tested on 80% confluent HDF cells over 24 h. Cell viabilities were then assessed via an MTT assay (3-(4,5-dimethylthiazol-2-yl)-2,5 diphenyl tetrazolium bromide) (Sigma-Aldrich, St Louis, Mo.). Cells were washed at 4° C. with cold PBS, then incubated with MTT solution (0.5 mg/ml MTT in PBS at 20° C., 1 ml per well of a 24-well plate) for 1 h at 37° C. in a humidified incubator (5% $CO_2$/95% air). For healthy viable cells, MTT is reduced to a purple formazan salt by the mitochondrial enzyme, succinyl dehydrogenase, which allows spectroscopic quantification of cell viability. After 1 h, the solution was aspirated and the insoluble intracellular formazan product was solubilized and removed from cells by adding acidified iso-propanol (0.30 ml per well of a 24-well plate), followed by incubation for 10 min. The absorbance at 540 nm was then determined using a plate reading visible absorption spectrophotometer, with the absorbance at 630 nm being used as a reference. Mean viability data and SEM were normalized to a negative control (no treatment, 100% viability) and expressed as a percentage viability±SEM. Experiments were performed in duplicate well samples with n=3 independent experiments. For statistical analysis, the student's paired t-test was used in the raw data to assess the significance of differences between the samples and the control group.

Results

Figure 16:
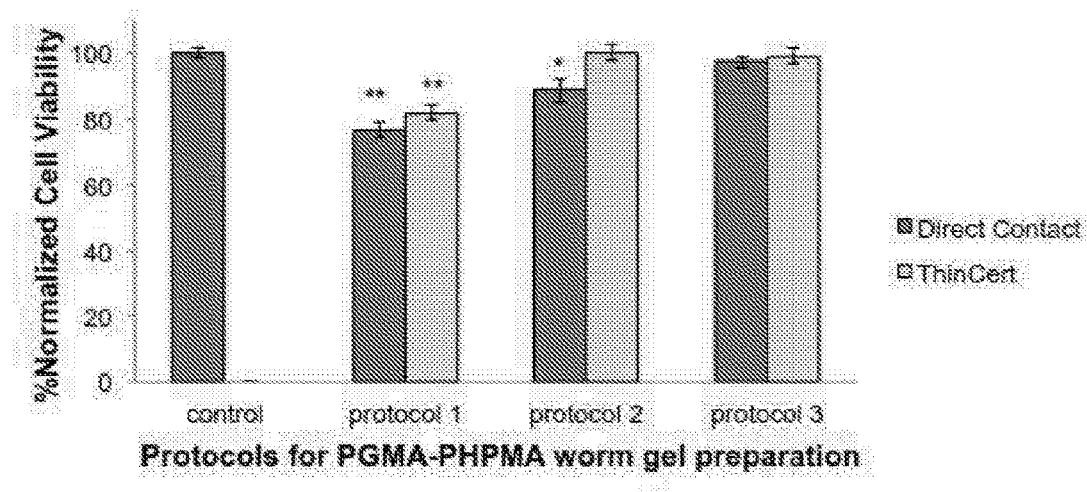
FIG. 16 shows optimization of HDF cell viabilities for $PGMA_{55}$-$PHPMA_{135}$ copolymer worm gels. Three protocols were evaluated for producing copolymer worm gels in cell culture media. Protocol 1 (20% w/v copolymer gel prepared in 150 mM PBS, diluted two-fold and dialyzed for two days against PBS), Protocol 2 (same as protocol 1, but with dialysis for 7 days), Protocol 3 (same as protocol 2, followed by freeze-drying overnight and redispersion in pure cell culture medium (DMEM). HDF cell viability was evaluated using both a direct contact assay with cell monolayers and also an indirect assay using ThinCert inserts. An MTT assay was used to assess cell viability at 37° C. Experiments were conducted in triplicate (N=3); **p<0.01, *p<0.05.

Using a polymerization-induced self-assembly (PISA) formulation, (Blanazs et al. *J Am Chem Soc*, 2012, 134, 9741-9748) PGMA-PHPMA diblock copolymer worm gels can be synthesized directly in either pure water or in physiological buffers such as PBS. In principle, PBS should promote cellular biocompatibility, hence initial formulations (see Protocol 1 above,) involved synthesis of $PGMA_{55}$-$PHPMA_{135}$ worm gels at 20% w/v solids in PBS followed by dialysis at 4° C. in its non-gelled form for 2 days against PBS (to ensure complete removal of any low molecular weight impurities), prior to dilution with the desired cell culture medium to afford a 6% w/v worm gel). Nevertheless, cell viability assays on human dermal fibroblast (HDF) cells suggested that this protocol does not allow optimal cell viability to be achieved (FIG. 16). In fact, both the direct contact and the indirect contact ThinCert assay indicated a significant reduction in cell viability (p<0.01), see FIG. 16. Thus a new approach (see Protocol 2 above) was developed whereby the $PGMA_{55}$-$PHPMA_{135}$ copolymer dispersion was subjected to dialysis for 7 days, rather than 2 days. Cell viability assays confirmed an improvement in performance, with ThinCert assays showing no significant differences compared to an untreated control group (see FIG. 16). However, the direct contact assay still indicated sub-optimal cell viability (p<0.05). This was not unexpected, since the cell medium was diluted two-fold with PBS when preparing such worm gels and hence not at its optimal concentration. To further optimize cell viability, a third protocol was devised (see Protocol 3 above) whereby the $PGMA_{55}$-$PHPMA_{135}$ copolymer worms were prepared in PBS at 20% w/v, dialyzed against pure water for 7 days and freeze-dried overnight to afford a dry powder, which could be redispersed in 100% cell culture media to reform free-standing transparent aqueous worm gels. This latter protocol produced hydrogels that exhibited very high cellular viabilities (FIG. 16) while maintaining the thermo-reversible gelation behavior desired for cell biology applications.

Example 8: Quantification of the Survival of hES Cell Colonies Using a Live/Dead Assay after their Long-Term Immersion in a $PGMA_{55}$-$PHPMA_{135}$ Worm Gel at 37° C., Followed by Cell Harvesting Via Degelation at 4° C.

% Colony Recovery Experiments

Figure 17:
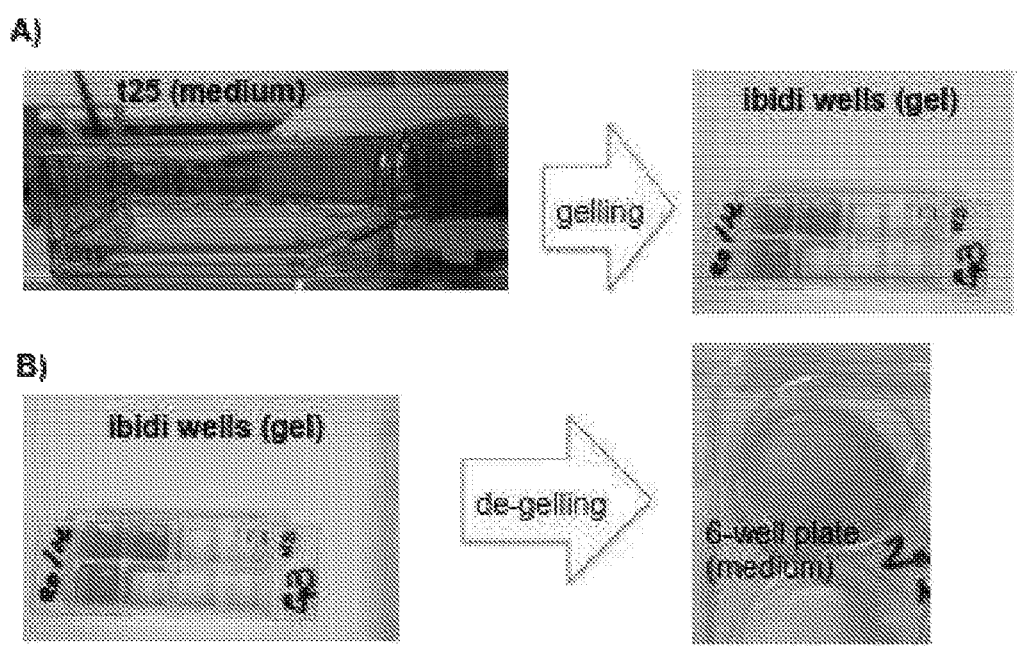
FIG. 17 shows the gelation/degelation process employed for hES cell colonies using $PGMA_{55}$-$PHPMA_{135}$ worm gels. A) Colonies grown in a Nutristem within t25 vessels were harvested mechanically and immediately gelled onto 8-well ibidi slides. Gels containing cell colonies were maintained at 37° C. in a humidified incubator (5% $CO_2$/95% air) over 7, 14 or 21 days. B) After each time point, the ibidi wells were placed onto ice for 5 minutes so as to induce gelation. Then the free-flowing cold copolymer dispersion containing the cell colonies was diluted approximately ten-fold into a Cellstart-treated 6-well plate containing Nutristem medium in order to release the colonies.

The hES cells were typically grown under xeno-free conditions using Nutristem cell culture medium (Stemgent, UK) and t25 vessels coated with Cellstart (Life Technologies, UK), unless otherwise stated. Cell cultures were maintained at 37° C. in a humidified incubator (5% $CO_2$/95% air) and the medium was renewed daily. When cultures achieved optimal cell density (typically 60-70% surface coverage), the cell medium was replenished and colonies were mechanically harvested with the aid of an optical microscope. Colonies were recovered from cell media and placed onto 35 mm Petri dishes in preparation for gel seeding. Ibidi 8-well slides were placed on ice and 500 µl of a cold 6% PGMA$_{55}$-PHPMA$_{135}$ copolymer dispersion (which is a free-flowing liquid at ~4° C.) was added to each of the wells. Using a sterile plastic Pasteur pipette equipped with a 'super-fine' tip, individual colonies were placed on the center of each ibidi well and gently stirred to allow mixing. Gelation (FIG. 17) was immediately triggered by placing the ibidi wells in a humidified incubator (5% $CO_2$/95% air) set at 37° C. Cell colonies were incubated for the desired time period (i.e. 7, 14 or 21 days) prior to harvesting. The number of colonies (typically 3-15) in each gelled well was determined using an optical microscope. Degelation (FIG. 17) was triggered by placing each ibidi slide on ice for approximately 5 min and the resulting cold free-flowing copolymer dispersion containing the cell colonies was diluted approximately ten-fold into a Cellstart-treated 6-well plate containing Nutristem (5.0 ml). This led to release of the colonies into the culture medium. The ibidi wells were inspected using an optical microscope and the number of colonies remaining in the wells (or colony loss) was recorded. The 6-well plates were stored for approximately 3 h in a humidified incubator (5% $CO_2$/95% air) to allow viable cell colonies to adhere to the Cellstart matrix. Subsequently, the medium was replenished daily and the colonies were monitored for up to 7 days, with the number of thriving colonies being recorded. The % colony recovery was calculated as the average colony recovery per time point±SEM normalized to the initial number of colonies prior to degelation. The % colony loss was similarly estimated. An internal control group was included in this study, whereby cell colonies were immersed in a worm gel for just 10 min. and then immediately harvested. This enabled the efficiency of the colony isolation and colony transfer protocols to be assessed. Experiments were performed in triplicate wells with n=3 independent experiments.

Live/Dead Assay

The viabilities of hES cell colonies immersed within PGMA$_{55}$-PHPMA$_{135}$ worm gels was assessed using a well-known commercial live/dead assay (Life Technologies, UK). This assay utilizes a binary mixture of a cell-permeable SYTO® 9 green fluorescent nucleic acid stain (ex 480 nm, em 500 nm) and an impermeable red fluorescent nucleic acid stain, propidium iodide (PI, ex 490 nm, em 635 nm). Cells with compromised (i.e. leaky) membranes are stained red (PI) and are designated as dead or dying, whereas cells with intact membranes are stained green (Syto-9) and designated as living. When used alone, the PI stain generally labels all cells, but when both dyes are present the PI penetrates damaged membranes and quenches the fluorescence due to Syto 9, so that its green signal is not detected. Briefly, the gelled colonies were cooled to around 4° C. for 5 minutes to trigger degelation and then allowed to sediment under gravity. The free-flowing aqueous copolymer dispersion supernatant was partially removed and colonies were washed once with cell culture medium pre-cooled to 4° C. The aqueous fluid was then removed and warm (37° C.) cell culture medium was added to each well containing Syto 9 (15 µM) and PI (60 µM). Cells were incubated in a humidified incubator (5% $CO_2$/95% air) for 25 min in order to allow dye uptake to occur. Then cell nuclei were counterstained for a further 5 min. with Hoechst 33342 (Life Technologies, UK). Finally, colonies were washed with PBS (pre-cooled to 4° C.) and further culture medium (depending on the vessel, typically 3 ml for a 6-well plate and 500 µl for ibidi imaging plates) was added, prior to inspection using a Nikon A1 confocal microscope equipped with an Okolab environmental control chamber for live cell studies.

Results

Figure 18:
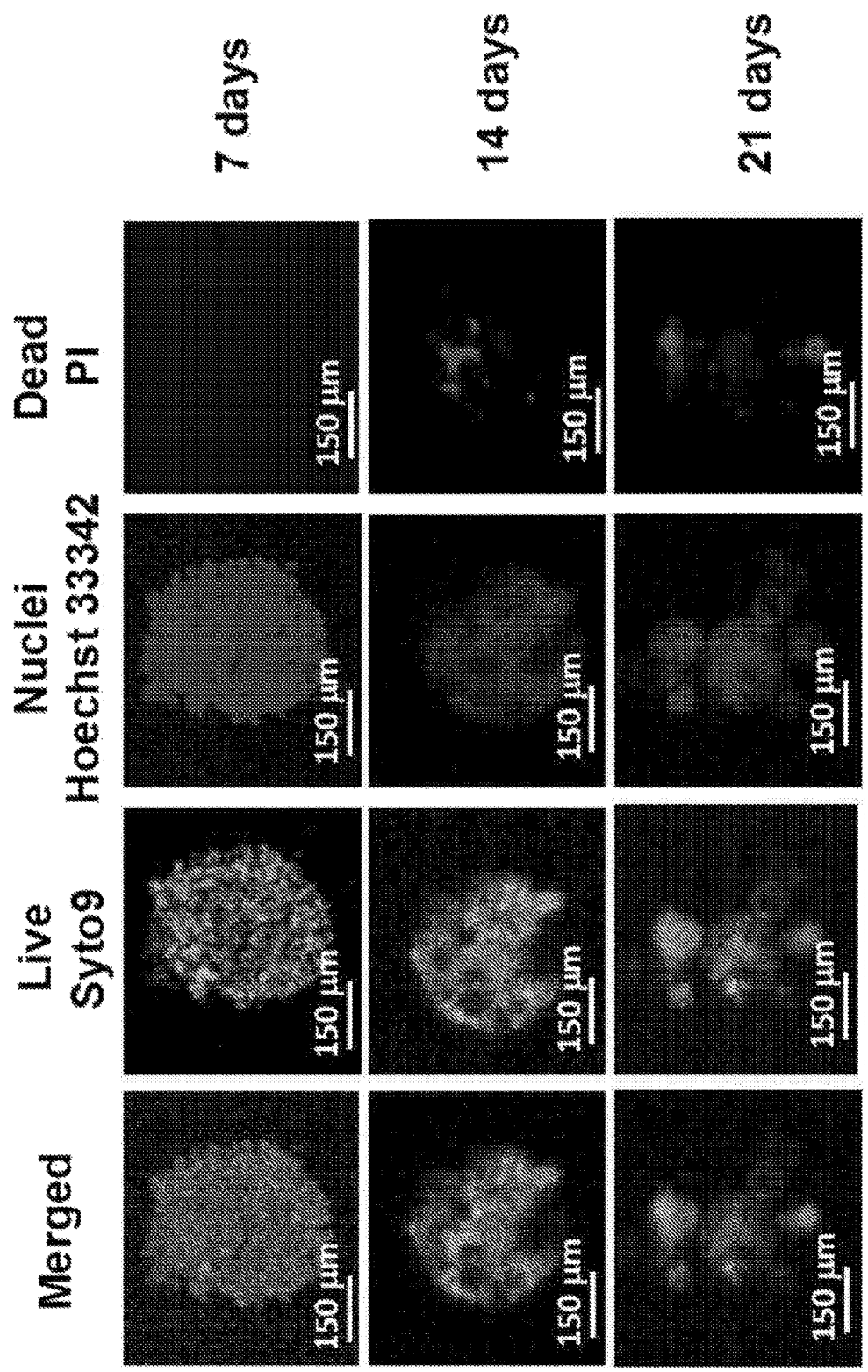
FIG. 18 shows live/dead imaging of hES cell colonies immersed within PGMA$_{55}$-PHPMA$_{135}$ worm gels using confocal microscopy. Representative fluorescence micrographs recorded after live/dead staining using Syto 9 and propidium iodide (PI) dyes for cell colonies immersed in a worm gel (prepared according to Protocol 3) for 7, 14 or 21 days at 37° C. The cell-permeable dye, Syto-9, reports on cell membrane integrity (live cells), whereas the cell-impermeable dye, PI, stains dead cells only. Hoechst 33342 was used a nuclei counter-stain.

A live/dead cell assay based on fluorescent dye retention combined with confocal microscopy enabled cells to be monitored for their viability while immersed within worm gels (see FIG. 18). After 7 days, all cell colonies displayed high viabilities with very little evidence for propidium iodide (PI, which selectively stains dead cells red) staining and mainly the green fluorescent marker (Syto 9) being observed. After 14 days immersion, some colonies contained areas of non-viable PI-stained cells (estimated to be <10% of the total area) but the majority of cells in colonies displayed good viability as indicated by the green fluorescence due to Syto 9 (FIG. 18). After 21 days immersion within the worm gel, a significant proportion of cell colonies still displayed at least some viable cells (see FIG. 18).

Figure 19:
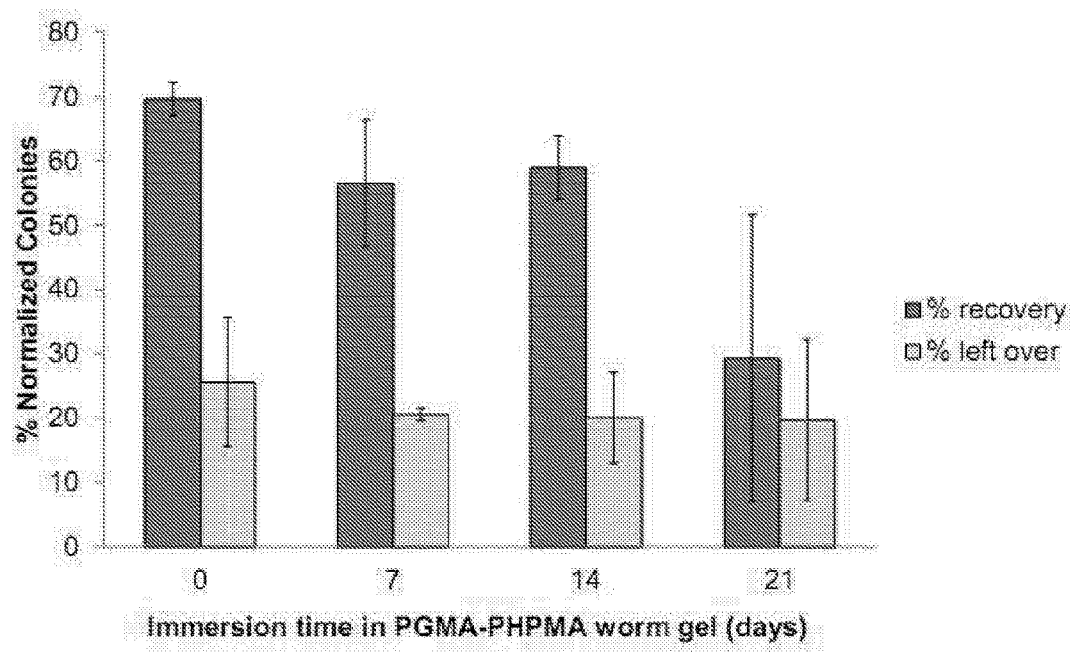
FIG. 19 shows recovery of hES cell colonies after their long-term storage at 37° C. in PGMA$_{55}$-PHPMA$_{135}$ worm gels prepared using Nutristem. The % colony recovery was calculated as an average colony recovery per time point (with the SEM being normalized to the initial number of colonies prior to degelation). The % colony loss was similarly estimated. An internal control group was also included in this study whereby colonies were immersed in a worm gel for approximately 10 min, cooled to 5° C. to induce degelation and subsequently isolated via centrifugation. Experiments were performed in triplicate well samples, with n=3 independent experiments.

To further assess the viability of cell colonies within these worm gels, the fraction of viable colonies recovered after degelation was determined (FIG. 19). It is known that the mechanics of colony detachment can compromise PSC viability (Heng et al., *Biotechnol Appl Biochem.* 2007, 47, 33-37), hence a control experiment (see FIG. 19, week 0) was conducted whereby cell colonies were immersed within the worm gel for just 10 minutes before being removed again via cold centrifugation. Approximately 70±3% of the harvested cell colonies were able to attach to Cellstart and proliferate. After 7 and 14 days 57±10% and 59±5% viable colonies were recovered, respectively.

Figure 20:
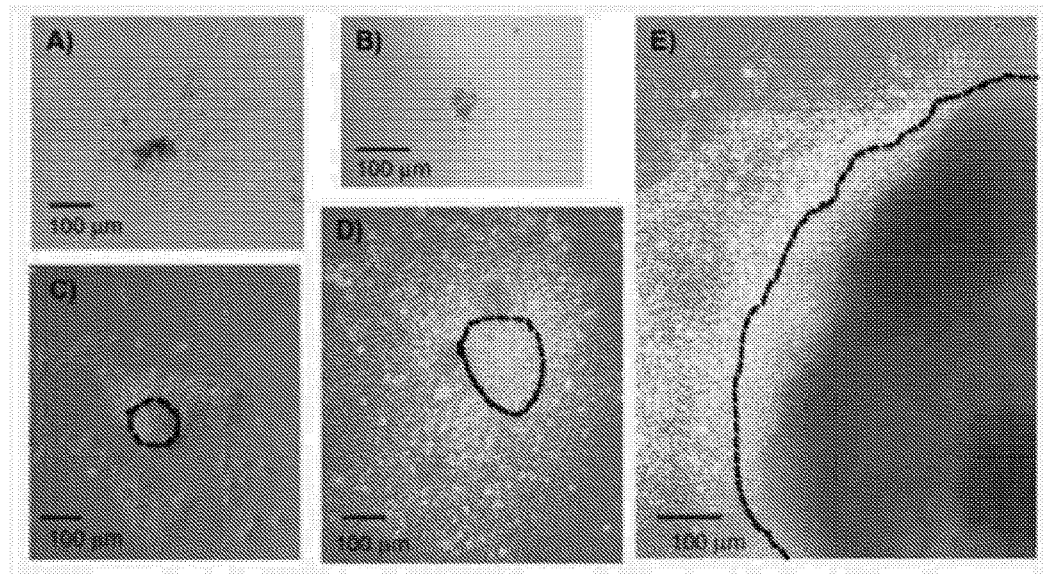
FIG. 20 shows the effect of original hES colony size on colony recovery after long-term storage for 14 days in a worm gel at 37° C., followed by isolation via degelation on cooling to 5° C. hESC colonies were dispersed mechanically in an aqueous PGMA-PHPMA worm gel comprising Nutristem cell culture medium and stored for 14 days at 37° C. Colonies were then isolated via degelation on cooling to 5° C. and subsequently plated on Cellstart and Nutristem liquid medium. (A)-(E) Optical micrographs recorded for various hES cell colonies 5 days after culture. Small colonies (<100 µm) either exhibited (A) minimal growth over time and differentiation or (B) failed to thrive after degelation. (C) Improved attachment and growth was obtained for colonies greater than 100 µm in size and (D) optimal growth was obtained for 100-200 µm colonies, which also exhibited the characteristic ES cell morphology. (E) Differentiated neuronal cells observed at the edge of a relatively large (>>200 µm) colony in a high-density culture. The traced line denotes the original colony size after initial degelation.

Since the colonies seeded for the % colony recovery experiments were disaggregated mechanically, it was difficult to achieve a uniform colony size distribution. It was found that the initial colony size had a significant effect on the outcome after isolation from the worm gel. If the colony size was less than 100 µm diameter, very few colonies adhered to Cell/Start and proliferated after isolation and this minor population either fully differentiated or did not thrive (FIGS. 20A and 20B). A better recovery rate was observed for colony sizes exceeding 100 µm (FIGS. 20C, 20D), with colonies ranging between 100 and 200 µm exhibiting the typical ES cell morphology (FIG. 20D). A similar influence of colony size on cell viability has been previously reported by other workers when using liquid culture media (Thomson, J. A., Itskovitz-Eldor, J., Shapiro, S. S., Waknitz, M. A., Swiergiel, J. J., Marshall, V. S. and Jones, J. M. *Science,* 1998, 282, 1145-1147; Reubinoff et al., *Nature Biotechnology* 2000, 18, 399-404. Interestingly, when relatively large (>>200 µm) colonies were immersed in a worm gel (FIG. 20E), they became significantly more dense on top, rather than spreading flat. Moreover, the edges of such colonies often exhibited some degree of neuronal differentiation, as judged by optical microscopy. Similar observations have been reported for high-density colonies dispersed in a liquid medium (Reubinoff et al., *Nature Biotechnology,* 2000, 18, 399-404.

Example 9: Experimental Evidence for Non-Proliferative Stasis (Suspended Animation)

DNA Extraction

Colonies were mechanically recovered from t25 flasks and placed on 35 mm Petri dishes prior to use. Each ibidi well was seeded with a fixed volume (500 µl) of cell colonies. This suspension was allowed to sediment for 5 min. and then the liquid medium was carefully removed. Then 6% PGMA-PHPMA copolymer dispersion (500 µl; pre-cooled to 40° C.) was added to each of the wells and gently stirred to allow mixing. Gelation was immediately triggered by placing the ibidi wells at 37° C. in a humidified incubator (5% $CO_2$/95% air). Cell colonies were then incubated for 7, 14 or 21 days. When required, degelation was triggered by placing each ibidi slide on ice for approximately 5 min. The contents of each well were then placed in labeled 1.5 ml Eppendorf tubes containing ice-cold PBS (1.0 ml). Samples were centrifuged twice at 4° C. for 5 min. (1000 rcf). Cell pellets were incubated using 100 µl of digestion buffer (comprising TE buffer (10 mM Tris pH 8 and 1 mM EDTA) plus 0.2% SDS) for 4 h at 37° C. Following this, a solvent mixture comprising 25:24:1 phenol:chloroform:isoamyl alcohol (100 µl) saturated with TE buffer was added to each Eppendorf tube and thoroughly mixed by vortex. The samples were centrifuged at 20° C. for 5 min. (14,000 rcf). Aqueous supernatants were then decanted and mixed with ice-cold ethanol (450 µl) and 3 M sodium acetate (50 µl). DNA was sedimented via centrifugation for 5 min. at 20° C. (14,000 rcf). Supernatants were carefully decanted and DNA pellets were dried in a 37° C. oven. Dried pellets were resuspended in TE buffer (20 µl). The DNA concentration was calculated by determining the absorbance at 260 nm using a Nanodrop spectrophotometer. Data were normalized with respect to an internal control group, whereby cell colonies were gelled for approximately 10 min. and then immediately harvested (day 0). Experiments were performed in duplicate wells with n=3 independent experiments.

ki67 Immunolabeling

Immunolabeling assays for ki67 were performed on both gelled colonies and recovered colonies (i.e. after thermally-induced degelation). The plated recovered colonies were directly washed twice with PBS and fixed for 30 min using an aqueous solution of 4% formaldehyde in PBS (750 µl). Colonies were isolated from the worm gels by incubation on ice for approximately 5 min. to induce degelation. Each well was then collected into 1.5 ml Eppendorf tubes containing ice-cold PBS (1 ml). Colonies were washed twice at 4° C. for 5 min. (1000 rcf) and then fixed for 30 min. using an aqueous solution of 4% formaldehyde in PBS (100 µl). All samples were then washed three times in PBS and permeabilized using a 0.1% Triton X100 PBS solution for 20 min. (1 mL per well in a 6-well plate and 100 µl per Eppendorf tube). Colonies were then washed three times in PBS and blocked in 5% BSA-PBS for 2 h at 20° C., prior to incubation with a primary antibody solution (1:1000 rabbit anti-human ki67 monoclonal antibody (Abcam)+1% BSA in PBS) overnight at 4° C. with gentle rocking. These antibody-labeled colonies were then washed three times in PBS and then incubated with a secondary antibody solution (1:1000 Goat anti-rabbit Cy3 IgG (abcam)+1% BSA in PBS) for 1 h at 20° C. with gentle rocking. Colonies were washed three times with PBS and cell nuclei were counter-stained for 5 min. with Hoechst 33342 (Life Technologies, UK). Finally, each sample was washed three times using PBS prior to inspection using an EVOS epifluorescence imaging system.

Results

Figure 21:
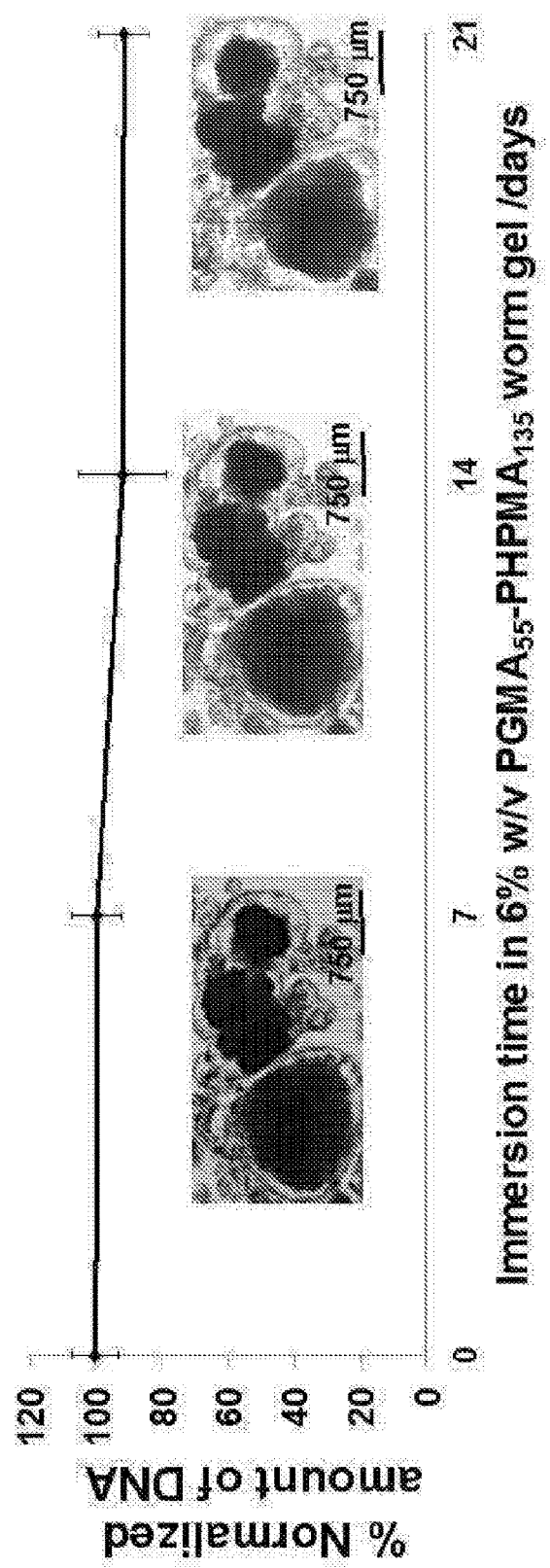
FIG. 21 shows a proliferation curve for hES cells immersed in a 6% w/v PGMA$_{55}$-PHPMA$_{135}$ worm gel for up to 21 days at 37° C. Colonies were harvested via degelation at the relevant time points (0, 7, 14 and 21 days) and total DNA was harvested and quantified, as described in Example 9. Data were normalized to the initial DNA amount (taken to be 100%) obtained from colonies seeded at day 0. Data represent average values of n=3 experiments conducted in duplicate wells. Optical microscopy images (see insets) indicated very little change in colony size over time, which is consistent with the observations of non-proliferation.
Figure 22:
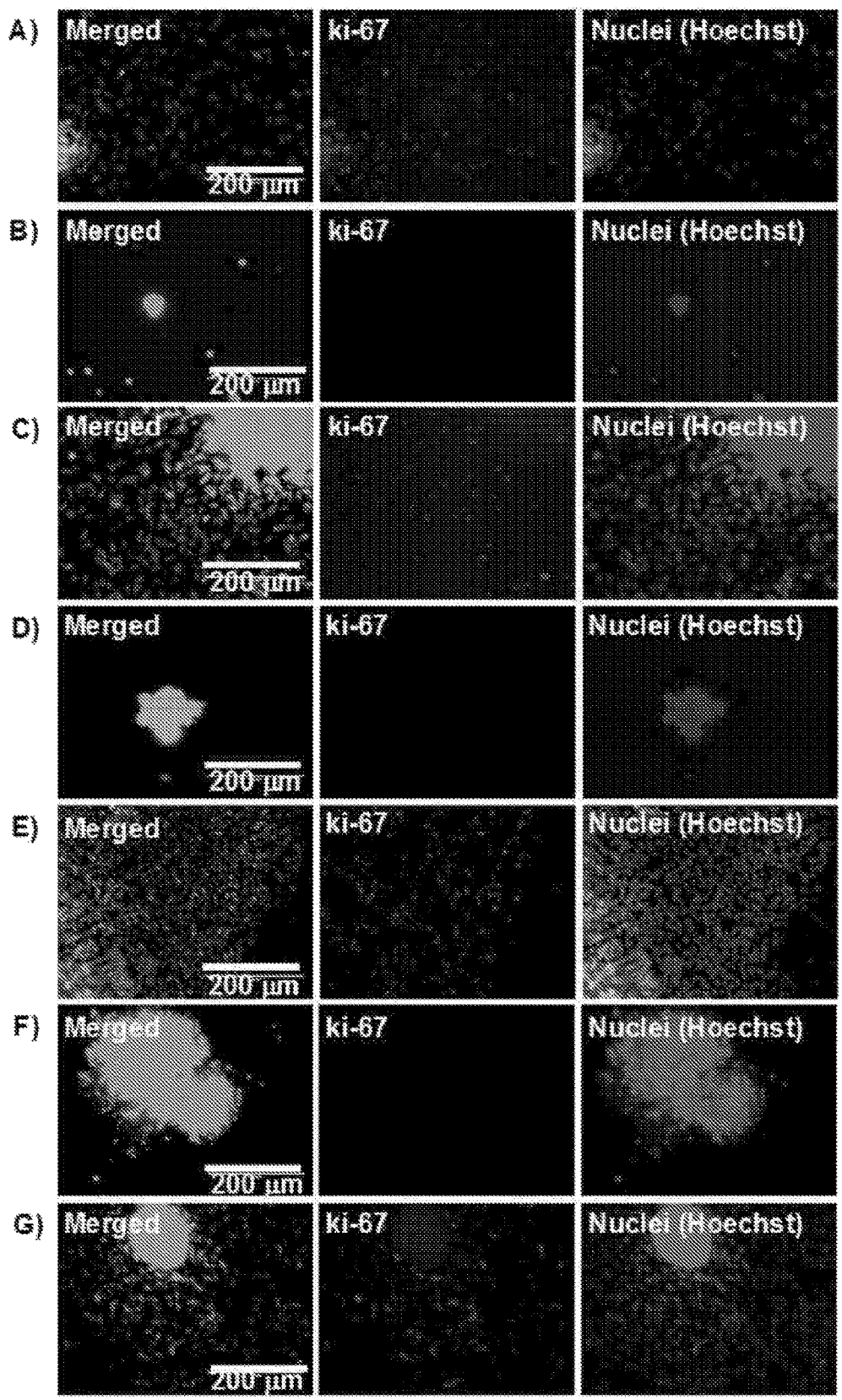
FIG. 22 shows immuno-labeling experiments, which were conducted as described in Example 9. (A) hES cell colonies were positively stained for ki-67 during normal proliferation in a liquid medium and a Cellstart matrix. Colonies were then mechanically removed and immersed in PGMA$_{55}$-PHPMA$_{135}$ worm gels containing Nutristem medium at 37° C. for (B) 7 days, (D) 14 days and (F) 21 days. While immersed within the worm gel, no ki-67 protein was detected for any of the cell colonies (B, D and F). Colonies were isolated via degelation after (C) 7 days, (E) 14 days and (G) 21 days, re-plated onto wells coated with Cellstart and grown in Nutristem medium for 5 days prior to conducting further immunolabeling experiments for ki-67. In all cases (see C, E and G), the presence of ki-67 was confirmed via positive staining (Cy3, red). Nuclei counter-stain (Hoechst 33342, blue). Experiments were performed in triplicate wells, with n=3 independent experiments.

Optical microscopy studies of hES colonies over time revealed almost no changes in colony size or number (see FIG. 21). Nevertheless, live/dead imaging and colony recovery data suggested that a relatively high fraction of the colonies remained viable following their long-term storage in worm gels (FIG. 18). To assess the extent of cell proliferation within the worm gels, colonies were harvested and the normalized amount (relative to day 0) of DNA extracted from cell nuclei was determined over time (see FIG. 21). No significant change in the total amount of DNA was detected, suggesting negligible proliferation of the cell colonies during their storage in the worm gels. Immunolabeling experiments (see FIG. 22) indicate that, once immersed in the worm gel, hES cells undergo cell cycle arrest at the G1/S checkpoint. The presence of ki-67 is a well-known marker for cell proliferation and this protein is present during each stage of the cell cycle (Scholzen and Gerdes *J Cell Physiol.* 2000, 182, 311-322). The absence of ki-67 in the gelled colonies is confirmed by selective staining experiments at every time point investigated, which suggests that the hES cells exit the cell cycle at $G_o$ and enter their dormant state, or stasis (see FIG. 22). In contrast, harvesting via degelation followed by adherence to an appropriate ECM matrix (i.e. Cellstart) enabled the colonies to re-enter the cell cycle (as judged by positive ki-67 staining) and regain their proliferative state (see FIG. 22). The $PGMA_{55}$-$PHPMA_{135}$ diblock copolymer worm gel contains no specific binding motifs to promote cell adhesion. Indeed, its multiple hydroxy functionality is known to reduce cell adhesion (Faucheux et al., *Biomaterials*, 2004, 25, 2721-2730; Arima et al., *J. Mater. Chem.*, 2007, 17, 4079-4087). Recently, it has been reported that hES cells utilize anoikis as (i) a cell death mechanism in the absence of cell adhesion (Watanabe et al., *Nature Biotechnology*, 2007, 25, 681-686) and (ii) a typical physiological event during differentiation (Coucouvanis and Martin *Cell*, 1995, 83, 279-287). Thus it is non-obvious that immersion of hES cells in such a bio-inert, non-interacting 3D matrix as these worm gels should lead to stasis, rather than anoikis.

Example 10: Transport Data

Recently, embryonic stem cell banks have been established worldwide. These banks play an important role in archiving and providing high-quality human and animal ES cells for the research community. These cell banks have efficiently generated numerous cryopreserved cell lines and genetically-engineered (i.e. reporter gene) cell lines and have supplied these strains to researchers requesting them. Cryopreservation is a critical step for the storage and transportation of human embryonic stem cells (ES cells) (*The International Stem cell banking Initiative, Stem Cell Rev and Rep*, 2009, 5, 301-314). Efficient cryopreservation methods must offer high thawing efficiencies and maintain both the pluripotency and differentiation potential of the cells. However, the transport of cryopreserved cells is relatively expensive and has many associated problems. For example, the receiving facility must have in place the skills and instruments required for the specific freezing and thawing protocols and optimizing the delivery time is critical (Shaw and Nakagata *Methods Mol Biol*, 2002, 180, 207-228). Moreover, sub-optimal freeze-thawing processes can cause significant damage to cells (Shaw and Nakagata *Methods Mol Biol*, 2002, 180, 207-228). Furthermore, the transportation of liquid nitrogen containers is strictly regulated by the International Air Transport Association (*IATA*0 (*IATA dangerous goods regulations manual 54th edition* (*International Air Transport Association, Product Code: BK-IATA*13, 2013), so alternative cheaper and safer transportation options are highly desirable. Often, research institutes exchange cells transporting them in $CO_2$-gassed cell culture vessels filled with liquid medium. Although this is potentially a useful alternative, ES cells in culture do not handle low temperature stress very well (Reubinoff et al. *Hum. Reprod.* 2001, 16, 2187-2194). Perhaps surprisingly, rather little research has been devoted to this subject, particularly given the potential commercial revenues for a growing ES cell market. For a product to be distributable locally, it should be able to survive for at least 24 h under transport conditions. If its survival time could be increased to 48 h, this would enable intercontinental delivery and survival for 72 h would in principle allow worldwide delivery.

Figure 23:
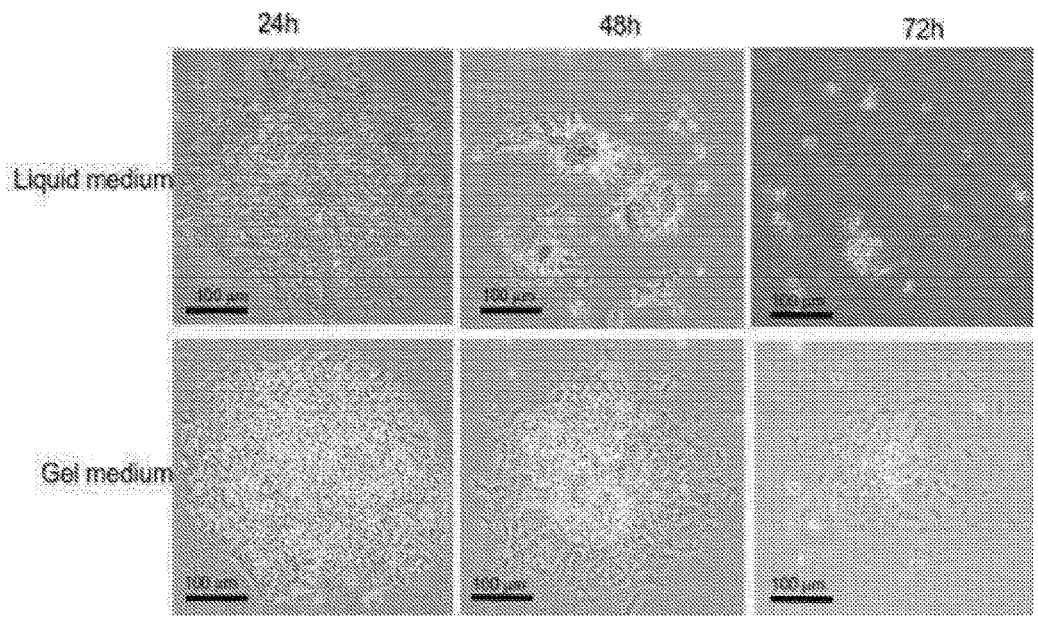
FIG. 23 shows hES cell colony recovery after storage at 18-22° C. for up to 72 h. After each time point (i.e. 24 h, 48 h or 72 h), hES cell colonies stored in liquid Nutristem were returned to normal cell culture conditions (37° C. in a humidified incubator (5% CO$_2$/95% air), whereas hES cell colonies stored within a 6% PGMA$_{55}$-PHPMA$_{135}$ worm gel were isolated via degelation, as previously described. Cell colonies were left overnight in the cell incubator to recover. Optical micrographs illustrate the typical appearance of cell colonies after a recovery period of 16 h.

A 6% $PGMA_{55}$-$PHPMA_{135}$ worm gel prepared using Nutristem was investigated as a potential transport medium for storage times of 24, 48 and 72 h (FIG. 23). As a control experiment, Nutristem was also used as a conventional cell culture medium in its liquid (i.e. non-gelled) form. In this case the cell colonies were attached to the bottom of individual Cellstart-coated 35 mm ibidi dishes. Cell colonies immersed in either the worm gel or the liquid Nutristem were equilibrated in a 5% $CO_2$-humidified incubator at 37° C. for 8 h prior to storage in a typical polystyrene transport box. During the hypothetical storage time, heated (37° C.) pads were added to the storage box to minimize heat losses over this time period. This enabled a temperature range of approximately 18 to 22° C. to be maintained, rather than 37° C. After each time point, the cells immersed in the liquid Nutristem were returned to normal cell culture conditions (i.e. 37° C. in a humidified incubator (5% $CO_2$/95% air), whereas the colonies within the worm gel were isolated via degelation (as previously described) and then allowed to adhere to the bottom of individual Cellstart-coated 35 mm ibidi dishes. The attached cell colonies were left overnight (approximately 16 h) in an incubator to recover and then optical images of these colonies were recorded (FIG. 23). Cell colonies in liquid Nutristem survived well for up to 24 h during the simulated transport storage conditions, with most colonies displaying typical hES morphologies. Similarly, the colonies immersed in the worm gel also recovered well after storage under the same conditions. However, cells stored in the liquid Nutristem exhibited signs of stress after 48 h. Colonies exhibited 'clumping' and the amount of detached debris increased, although some colonies still remained attached. (FIG. 23). In contrast, cell colonies stored within the worm gel recovered relatively well after 48 h, and retained their characteristic morphology, but significantly fewer viable colonies were recovered compared to those isolated after 24 h. No viable colonies could be recovered from the liquid Nutristem after 72 h; all colonies appeared detached and clumped (FIG. 23). However, a few viable cell colonies could still be recovered after 72 h storage within the worm gel (FIG. 23).

Example 11: Storage of Individual hES Cells within Worm Gels

Figure 24:
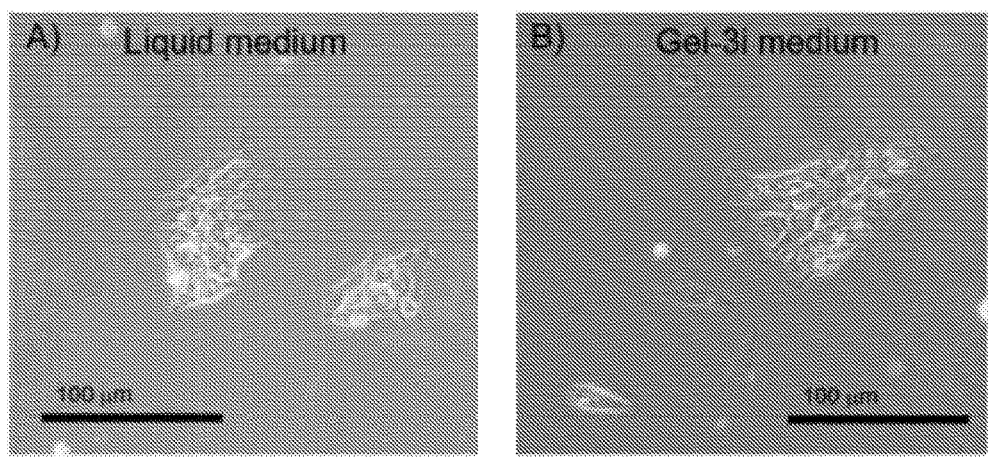
FIG. 24 shows hES cell recovery after 24 h storage at 37° C. within a conventional liquid 3i cell culture medium or a 6% PGMA$_{55}$-PHPMA$_{135}$ worm gel prepared using the same 3i medium. (A) Suspensions of individual hES cells stored within a conventional liquid 3i medium for 24 h at 37° C. were cultured on Cellstart-coated 6-well plates. (B) hES cells immersed within a 6% PGMA$_{55}$-PHPMA$_{135}$ worm gel were isolated via degelation after storage for 24 h at 37° C. in a humidified incubator (5% CO$_2$/95% air) and plated on Cellstart coated 6-well plates. Cell cultures were allowed to adhere onto Cellstart-coated 6-well plates for 16 h and then examined by optical microscopy. Regardless of their storage conditions, the characteristic morphology associated with pluripotent stem cells was observed.

Use of a worm gel to preserve a suspension of individual hES cells (rather than hES colonies) was investigated. Suspensions of individual hES cells were cultured and then gelled within a 6% $PGMA_{55}$-$PHPMA_{135}$ worm gel prepared using 3i medium. This particular medium contains specific anoikis inhibitors that favor individual hES cell culture (Gafni et al., *Nature*. 2013, 504(7479), 282-286). Briefly, each t25 vessel containing hES cells in culture was washed once with PBS and then cell dissociation solution (1.50 ml, Sigma-Aldrich) was added. After incubation for 3 min at 37° C. in a humidified incubator (5% $CO_2$/95% air), the suspension of individual cells was harvested by adding 3i cell culture medium (1.5 ml), followed by centrifugation at 1000 rcf for 5 min. at 20° C. The pellets were resuspended either in liquid 3i medium (1.5 ml) or in a cold free-flowing copolymer dispersion (prepared using 3i medium) at 40° C. that quickly formed a worm gel on warming to 37° C. Cells in liquid 3i medium were cultured on Cellstart-coated 6-well plates, whereas cells stored within the worm gel plus 3i medium were isolated via degelation after 24 h at 37° C. in a humidified incubator (5% $CO_2$/95% air) and then allowed to adhere on Cellstart-coated 6-well plates. After 16 h, the cells were examined by optical microscopy (FIG. 24). Cells recovered from the liquid 3i medium and the worm gel plus 3i medium displayed similar sizes, morphologies and surface coverages after their recovery. Thus the 6% $PGMA_{55}$-$PHPMA_{135}$ worm gel can be used to store suspensions of individual hES cells without any discernible detrimental effects.

Example 11: Rheological Studies

Rheology studies were conducted on 6% w/v $PGMA_{55}$-$PHPMA_{135}$ copolymer worm gels in various aqueous media using an AR-G2 rheometer (TA instruments) equipped with a variable temperature Peltier plate and a 40 mm 2° aluminium cone.

Figure 25:
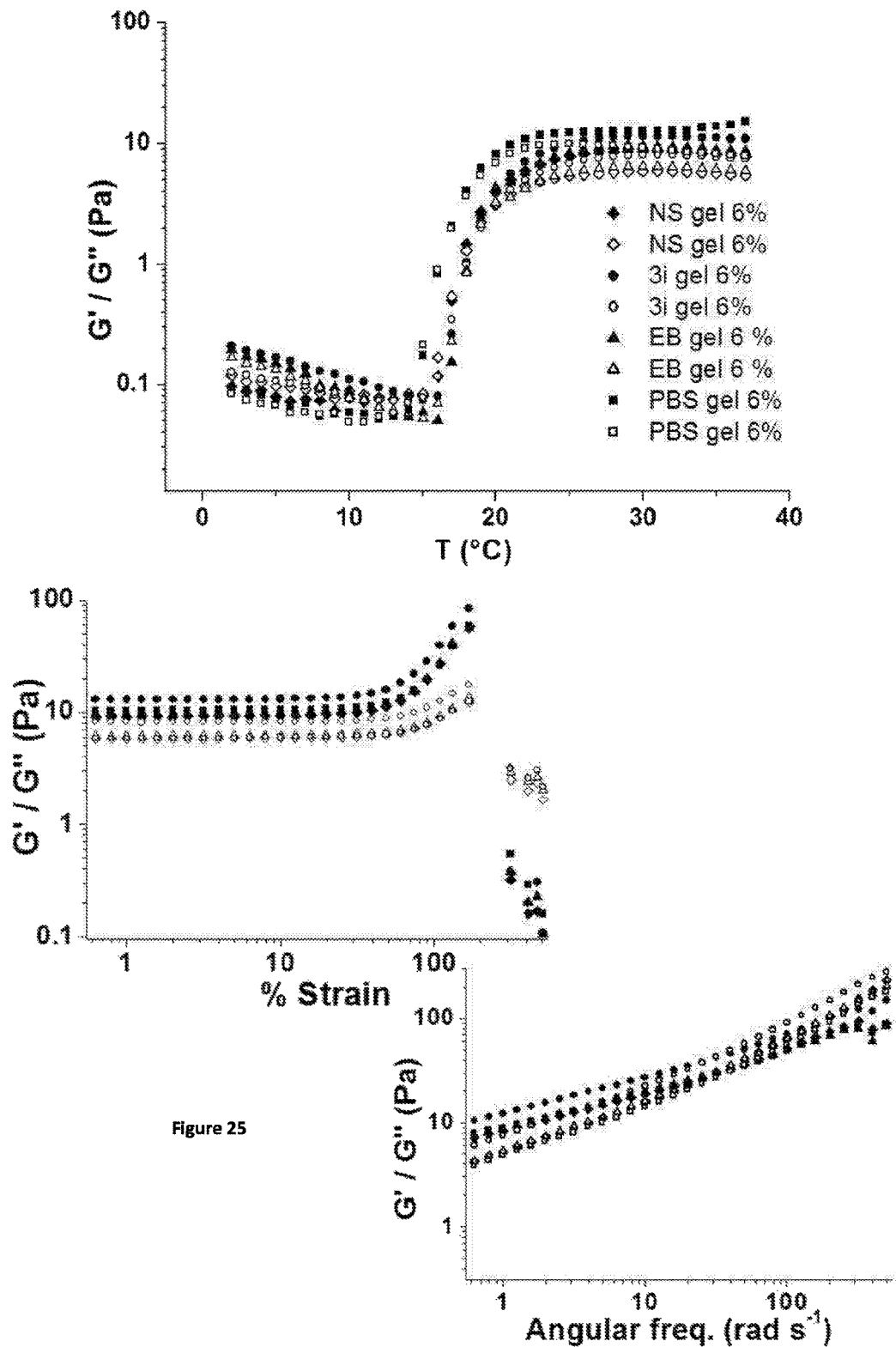
FIG. 25 shows (a) temperature dependence of the gel strength (G', G") on cooling a 6% w/v PGMA$_{55}$-PHPMA$_{135}$ worm gel (prepared by dispersing the freeze-dried copolymer powder into various aqueous media at 4° C. according to Protocol 3; see labels for details) from 37° C. to 2° C. at an applied strain of 1.0% and a fixed angular frequency of 1.0 rad s$^{-1}$. (b) Variation in gel strength (G', G") with applied strain at 37° C. at an angular frequency of 1 rad s$^{-1}$. (c) Variation in gel strength (G', G") with angular frequency (at a fixed applied strain of 1.0%) for 6% w/v PGMA$_{55}$-PHPMA$_{135}$ worm gel in various cell culture media.

For the three types of cell culture media (e.g. PBS, EB (Embryoid body medium, Millipore), NS (Nutristem medium, Stemgent) or 3i medium (Gafni et al., *Nature*. 2013, 504(7479), 282-286), no significant differences were observed in either the gel strength ($G'\sim10^1$ Pa) or the critical gelation temperature (CGT~18° C.). The CGT for the worm gel prepared using PBS was slightly lower (17° C.) but its thermo-reversible behavior is otherwise broadly similar. Strain sweeps (FIG. 25b) for each gel produced comparable G' values (9 to 13 Pa), with deviation from the linear viscoelastic region occurring at around 60% applied strain in all cases. Angular frequency sweeps (FIG. 25c) were also broadly comparable; indicating that varying the cell culture medium has only a relatively modest effect on the worm gel rheology.

The invention claimed is:

1. A medium for stem cells, the medium comprising: 1-30% w/w particles of a synthetic thermo-responsive copolymer dispersed in 70-99% w/w of an aqueous vehicle;
   wherein the medium is capable of undergoing a change between a non-gelatinous form and a gelatinous form in response to a change in temperature and, in the non-gelatinous form, the medium comprises a colloidally stable aqueous dispersion of the particles of the synthetic thermo-responsive copolymer and, in the gelatinous form, the medium is in the form of a gel that provides a scaffold or matrix capable of accommodating stem cells;
   and wherein the aqueous vehicle further comprises nutrients for maintaining the viability of stem cells;
   wherein the thermo-responsive copolymer comprises at least one hydrophilic polymeric block $P_1$, derived from a monomer $M_1$, and at least one hydrophobic polymeric block $P_2$ which represents a substantially aqueously insoluble polymeric component derived from an aqueously soluble RAFT monomer $M_2$; wherein the RAFT monomer $M_2$ is a monomer capable of undergoing a Reversible Addition-Fragmentation chain Transfer (RAFT)-type polymerization process via RAFT polymerization.

2. The medium of claim 1, wherein the medium exists in the non-gelatinous form at temperatures below a gelling temperature and in a gelatinous form at temperatures above the gelling temperature of the medium, and the medium is in the gelatinous form at temperatures greater than or equal to 20° C.

3. The medium of claim 1, wherein the particles of the synthetic thermo-responsive co-polymer are of a substantially spherical shape when the medium is in the non-gelatinous form, and are substantially anisotropic worms or worm-like particles when the medium is in the gelatinous form.

4. The medium of claim 1, wherein the thermo-responsive copolymer is defined by Formula B:

Formula B wherein $P_1$ represents a polymeric component derived from a monomer $M_1$ and $P_2$ represents a substantially aqueously insoluble polymeric component derived from an aqueously soluble monomer $M_2$.

5. The medium of claim 4, wherein:

Each monomer $M_1$ is selected from a monomer of the Formula $M_{1A}$, $M_{1B}$, and/or $M_{1C}$:

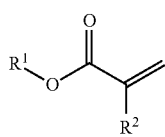

Formula $M_{1A}$

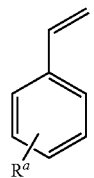

Formula $M_{1B}$

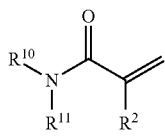

Formula $M_{1C}$ where $R^1$, $R^{10}$ and $R^{11}$ represent a substituent of $M_{1A}$ or $M_{1C}$ which allows $P_1$ to be at least partially aqueously soluble, $R^2$ represents H, $CH_3$ or CN, $R^S$ represents one or more substituents of the aromatic ring effective to allow $P_1$ to be at least partially aqueously soluble, and each monomer $M_2$ is selected from a monomer of the Formulae

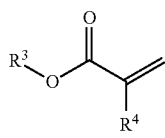

Formula $M_{2A}$

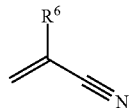

Formula $M_{2B}$ $M_{2A}$ and/or $M_{2B}$;

Where $R^3$ is a substituent of $M_2$ which allows $P_2$ to be substantially aqueously insoluble, and $R^4$ and $R^6$ independently represent H or methyl;

or $P_1$ is a copolymer comprising monomer $M_2$ with a monomer $M_2$ provided that the polymer $P_1$ remains at least partially aqueously soluble.

6. The medium of any of claim 4 or 5, wherein $P_1$ is a polymer or co-polymer comprising glycerol monomethacrylate (GMA) monomeric units, and $P_2$ is a polymer or copolymer comprising 2-hydroxypropyl methacrylate (HPMA) monomeric units.

7. The medium of claim 6, wherein the thermo-responsive copolymer is a block copolymer of Formula B [$P_1$-$P_2$] selected from the group consisting of:

PGMA-PHPMA, wherein the PGMA block has a degree of polymerization between 20 and 200; and the PHPMA block has a degree of polymerization between 50 and 300;

PGMA-P (GMA-HPMA), wherein the PGMA block has a degree of polymerisation (DP) of 10 to 120, and the P (GMA-HPMA) block may suitably have a degree of polymerisation (DP) of between 20 and 200; and PGMA-P (DEGMA-HPMA), wherein the PGMA block has a degree of polymerisation between 20 and 200; the P (DEGMA-HPMA) block has a degree of polymerisation (DP) between 20 and 200; and the ratio of DEGMA to HPMA monomer units within the P (DEGMA-HPMA) block is between 10: and 1:10.

8. The medium of claim 1, wherein the stem cells are mammalian stem cells.

9. A kit for preparing the medium of claim 1, the kit comprising:
particles of a synthetic thermo-responsive copolymer; and
an aqueous vehicle for maintaining the viability of stem cells.

10. A method of storing or preserving one or more stem cells, the method comprising:
contacting a non-gelatinous form of the medium of claim 1 with one or more stem cells to produce a fluid stem cell composition;
changing the temperature of the medium to cause the medium to change from the non-gelatinous form to the gelatinous form and thereby produce a gelled stem cell composition; and
storing the gelled stem cell composition.

11. The method of claim 10, wherein step (i) is performed with the stem cell medium at a temperature of at or below 10° C.; and step (ii) comprises adjusting the temperature of the stem cell matrix from at or below 10° C. up to or above 18° C.

12. A stem cell composition comprising one or more stem cells dispersed within the medium of claim 1.

13. The stem cell composition of claim 12, wherein the stem cells are mammalian stem cells.

14. A method of releasing one or more stem cells from a gelled stem cell composition, the method comprising:

providing a gelled stem cell composition comprising one or more stem cells dispersed within a gelatinous form of the medium of claim 1;

changing the temperature of the stem cell medium to cause the medium to change from the gelatinous form to the non-gelatinous form to thereby produce a fluid stem cell composition; and optionally thereafter isolating said stem cells from the fluid stem cell composition.

15. The medium as claimed in claim 1, wherein transition between the non-gelatinous form and the gelatinous form, and vice versa, of the medium is a phase transition due to a temperature-dependent change in the morphology of the particles of a synthetic thermo-responsive co-polymer.

16. The medium as claimed in claim 1, wherein the particles of synthetic thermo-responsive co-polymer are micellar particles within the aqueous vehicle, and the synthetic thermo-responsive co-polymer is defined by Formula B:

$$[P_1\text{---}P_2] \quad \text{Formula B}$$

wherein $P_1$ and $P_2$ are distinct polymeric chains within the co-polymer, $P_1$ being hydrophilic relative to $P_2$ such that $P_1$ is a stabilizer chain and $P_2$ is a core-forming chain, wherein $P_2$ is thermo-responsive.

17. The medium as claimed in claim 1, wherein in the non-gelatinous form of the medium, the particles of the thermo-responsive copolymer are nanoparticles that are less than 500 nm in size.

18. The medium as claimed in claim 1, wherein the medium is an ultra-filtrated medium filtered via a 0.01-1 μm filter.

19. The medium as claimed in claim 1, wherein the particles of the synthetic thermo-responsive co-polymer are present within the aqueous vehicle at a concentration of 2-12 wt %.

20. The medium as claimed in claim 1, wherein the particles of the synthetic thermo-responsive co-polymer are present within the aqueous vehicle at a concentration of 3-7 wt %.

21. The medium of claim 1, wherein $P_1$ is a copolymer, which comprises two or more monomers $M_1$.

22. The medium of claim 1, wherein $P_1$ is a homopolymer comprising a single monomer $M_1$.

23. The medium of claim 1, wherein $P_2$ is a homopolymer comprising a single monomer $M_2$.

24. The medium of claim 1, wherein $P_2$ additionally comprises a cross-linking monomeric unit whether $P_2$ is a copolymer or a homopolymer.

25. A medium for stem cells, the medium comprising: 1-30% w/w particles of a synthetic thermo-responsive co-polymer dispersed in 70-99% w/w of an aqueous vehicle;

wherein the medium is capable of undergoing a change between a non-gelatinous form and a gelatinous form in response to a change in temperature and, in the non-gelatinous form, the medium comprises a colloidally stable aqueous dispersion of the particles of the synthetic thermo-responsive copolymer and, in the gelatinous form, the medium is in the form of a gel that provides a scaffold or matrix capable of accommodating stem cells;

wherein the aqueous vehicle further comprises nutrients for maintaining the viability of stem cells; and wherein the thermo-responsive copolymer is defined by Formula B:

$$[P_1\text{---}P_2] \quad \text{Formula B}$$

wherein $P_1$ represents a polymeric component derived from a monomer $M_1$ and $P_2$ represents a substantially aqueously insoluble polymeric component derived from an aqueously soluble monomer $M_2$.

26. A medium for stem cells, the medium comprising: 1-30% w/w particles of a synthetic thermo-responsive co-polymer dispersed in 70-99% w/w of an aqueous vehicle;

wherein the medium is capable of undergoing a change between a non-gelatinous form and a gelatinous form in response to a change in temperature and, in the non-gelatinous form, the medium comprises a colloidally stable aqueous dispersion of the particles of the synthetic thermo-responsive copolymer and, in the gelatinous form, the medium is in the form of a gel that provides a scaffold or matrix capable of accommodating stem cells;

wherein the aqueous vehicle further comprises nutrients for maintaining the viability of stem cells; and wherein the particles of synthetic thermo-responsive co-polymer are micellar particles within the aqueous vehicle, and the synthetic thermo-responsive co-polymer is defined by Formula B:

$$[P_1\text{---}P_2] \quad \text{Formula B}$$

wherein $P_1$ and $P_2$ are distinct polymeric chains within the co-polymer, $P_1$ being hydrophilic relative to $P_2$ such that $P_1$ is a stabilizer chain and $P_2$ is a core-forming chain, wherein $P_2$ is thermo-responsive.

27. The medium of claim 25, wherein:

each monomer $M_1$ is selected from a monomer of the Formula $M_{1A}$, $M_{1B}$ and/or $M_{1C}$:

Formula $M_{1A}$

Formula $M_{1B}$

Formula $M_{1C}$ where $R^1$, $R^{10}$ and $R^{11}$ represents a substituent of $M_{1A}$ or $M_{1C}$ which allows $P_1$ to be at least partially aqueously soluble, $R^2$ represents H, $CH_3$ or CN, $R^s$ represents one or more substituents of the aromatic ring effective to allow $P_1$ to be least partially aqueously soluble, and each monomer $M_2$ is selected from a monomer of the Formulae

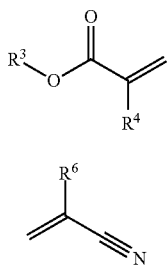

Formula $M_{2A}$

Formula $M_{2B}$ $M_{2A}$ and/or $M_{2B}$:

Where $R^3$ is a substituent of $M_2$ which allows $P_2$ to be substantially aqueously insoluble, and $R^4$ and $R^6$ independently represent H or methyl;

or $P_1$ is a copolymer comprising monomer $M_2$ with a monomer $M_2$ provided that the polymer $P_1$ remains at least partially aqueously soluble.

28. The medium of claim 25, wherein $P_1$ is a polymer or co-polymer comprising glycerol monomethacrylate (GMA) monomeric units, and $P_2$ is a polymer or copolymer comprising 2-hydroxypropyl methacrylate (HPMA) monomeric units.

29. The medium of claim 25, wherein the thermo-responsive copolymer is a block copolymer of Formula B [$P_1$-$P_2$] selected from the group consisting of:

PGMA-PHPMA, wherein the PGMA block has a degree of polymerization between 20 and 200; and the PHPMA block has a degree of polymerization between 50 and 300;

PGMA-P (GMA-HPMA), wherein the PGMA block has a degree of polymerisation (DP) of 10 to 120, and the P (GMAHPMA) block may suitably have a degree of polymerisation (DP) of between 20 and 200; and PGMA-P (DEGMA-HPMA), wherein the PGMA block has a degree of polymerisation between 20 and 200; the P (DEGMA-HPMA) block has a degree of polymerisation (DP) between 20 and 200; and the ratio of DEGMA to HPMA monomer units within the P (DEGMA-HPMA) block is between 10:1 and 1:10.

* * * * *